(12) United States Patent
Butler et al.

(10) Patent No.: US 10,682,464 B2
(45) Date of Patent: Jun. 16, 2020

(54) DRIVE MECHANISM OF AN INJECTION DEVICE

(71) Applicant: Sanofi, Paris (FR)

(72) Inventors: Joseph Butler, Rugby (GB); Paul Richard Draper, Evesham (GB)

(73) Assignee: Sanofi, Paris (FR)

( * ) Notice: Subject to any disclaimer, the term of this patent is extended or adjusted under 35 U.S.C. 154(b) by 166 days.

(21) Appl. No.: 15/517,827

(22) PCT Filed: Oct. 6, 2015

(86) PCT No.: PCT/EP2015/072980
§ 371 (c)(1),
(2) Date: Apr. 7, 2017

(87) PCT Pub. No.: WO2016/055438
PCT Pub. Date: Apr. 14, 2016

(65) Prior Publication Data
US 2017/0304537 A1    Oct. 26, 2017

(30) Foreign Application Priority Data
Oct. 9, 2014    (EP) ..................................... 14306597

(51) Int. Cl.
*A61M 5/20* (2006.01)
*A61M 5/315* (2006.01)
(Continued)

(52) U.S. Cl.
CPC ............ *A61M 5/20* (2013.01); *A61M 5/3157* (2013.01); *A61M 5/31541* (2013.01);
(Continued)

(58) Field of Classification Search
CPC ................ A61M 5/20; A61M 5/31543; A61M 5/31583; A61M 5/24; A61M 5/31551;
(Continued)

(56) References Cited

U.S. PATENT DOCUMENTS

| 8,398,593 B2 * | 3/2013 | Eich .................. A61M 5/31583 |
| | | 604/131 |
| 8,992,487 B2 * | 3/2015 | Eich ........................ A61M 5/20 |
| | | 604/207 |

(Continued)

FOREIGN PATENT DOCUMENTS

| CN | 102639171 | 8/2012 |
| CN | 103547304 | 1/2014 |

(Continued)

OTHER PUBLICATIONS

International Preliminary Report on Patentability in International Application No. PCT/EP2015/072980, dated Apr. 11, 2017, 8 pages.

(Continued)

*Primary Examiner* — Kevin C Sirmons
*Assistant Examiner* — Alexandra Lalonde
(74) *Attorney, Agent, or Firm* — Fish & Richardson P.C.

(57) ABSTRACT

A drive mechanism of an injection device for setting and dispensing of a dose of a medicament includes a body accommodating a cartridge filled with a medicament, an insert axially displaceable inside the body between a proximal operating position and a distal reset position, a piston rod to operably engage with a piston of the cartridge, a drive sleeve rotationally coupled with the piston rod and is rotationally lockable to the body for setting of a dose and rotationally releasable from the body for dispensing of a dose, respectively. The drive sleeve is axially displaceable relative to the body from a proximal operating position into a distal reset position through an axial connection of the insert and the drive sleeve, where the drive sleeve is rotationally released from the body when in the distal reset position.

19 Claims, 8 Drawing Sheets

(51) Int. Cl.
*A61M 5/31* (2006.01)
*A61M 5/24* (2006.01)

(52) U.S. Cl.
CPC .... *A61M 5/31543* (2013.01); *A61M 5/31553* (2013.01); *A61M 5/31583* (2013.01); *A61M 5/24* (2013.01); *A61M 2005/3126* (2013.01); *A61M 2005/3154* (2013.01); *A61M 2205/127* (2013.01); *A61M 2205/581* (2013.01); *A61M 2205/582* (2013.01)

(58) Field of Classification Search
CPC .......... A61M 5/31541; A61M 5/31535; A61M 5/31565; A61M 5/31576; A61M 5/31585; A61M 5/31586; A61M 5/31545; A61M 5/31548; A61M 5/3155; A61M 5/31553
See application file for complete search history.

(56) References Cited

U.S. PATENT DOCUMENTS

| | | | |
|---|---|---|---|
| 2004/0210199 A1* | 10/2004 | Atterbury | A61M 5/31535 604/224 |
| 2006/0153693 A1 | 7/2006 | Fiechter et al. | |
| 2009/0247951 A1 | 10/2009 | Kohlbrenner et al. | |
| 2011/0054412 A1* | 3/2011 | Eich | A61M 5/20 604/207 |
| 2011/0077595 A1* | 3/2011 | Eich | A61M 5/31501 604/135 |
| 2015/0148754 A1* | 5/2015 | Eich | A61M 5/20 604/235 |
| 2016/0158445 A1* | 6/2016 | Eich | A61M 5/20 604/235 |

FOREIGN PATENT DOCUMENTS

| | | |
|---|---|---|
| CN | 103648558 | 3/2014 |
| DE | 102004063652 | 7/2006 |
| JP | 2006-187628 | 7/2006 |
| JP | 2010-503430 | 2/2010 |
| JP | 2012-528631 | 11/2012 |
| WO | WO 2008/031235 | 3/2008 |
| WO | WO 2009/105909 | 9/2009 |
| WO | WO 2010/139643 | 12/2010 |
| WO | WO 2011/154481 | 12/2011 |
| WO | WO 2012/173553 | 12/2012 |
| WO | WO 2013/119132 | 8/2013 |

OTHER PUBLICATIONS

International Search Report and Written Opinion in International Application No. PCT/EP2015/072980, dated Jan. 29, 2016, 11 pages.

* cited by examiner

DRIVE MECHANISM OF AN INJECTION DEVICE

CROSS-REFERENCE TO RELATED APPLICATIONS

This application is a U.S. national stage application under 35 USC § 371 of International Application No. PCT/EP2015/072980, filed on Oct. 6, 2015, which claims priority to European Patent Application No. 14306597.7 filed on Oct. 9, 2014, the entire contents of which are incorporated herein by reference.

TECHNICAL FIELD

The present invention relates to a drive mechanism of a drug delivery device and to a drive mechanism of an injection device, such like an injection pen. In particular, the invention relates to a resetable drive mechanism of a reusable injection device that allows and enables a user of the device to reset the drive mechanism when an empty cartridge of the device is to be replaced by a new one.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod adapted to operably engage with a piston of the cartridge. By means of the drive mechanism and its piston rod, the piston of the cartridge is displaceable in a distal or dispensing direction to expel a predefined amount of the medicament via a piercing assembly, which is to be releasably coupled with a distal end section of the housing of the injection device.

The medicament to be dispensed by the injection device is typically provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be entirely discarded when the medicament in the cartridge has been dispensed or used-up.

Reusable devices typically comprise an access opening to remove an empty cartridge and to insert a filled or new cartridge into the device instead. Some injection devices comprise a multi-component housing, e.g. a proximally-located body that is releasably engaged with a distal cartridge holder. While the body accommodates and contains the mechanical components of a drive mechanism the cartridge holder accommodates the replaceable cartridge and keeps the cartridge in a well-defined position in regard to the drive mechanism, in particular in regard to the piston rod. A distal end of the cartridge holder or of the housing of the injection device is releasably connectable with a piercing assembly, typically comprising a double-tipped injection needle that is configured and designed to pierce a distal seal of the cartridge in order to obtain access to the interior thereof for expelling of a well-defined amount of the medicament from the cartridge through the distally-directed advancing motion of the piston rod.

Many injection devices, of e.g. pen-injector type, provide multiple and frequent dispensing and injection of the liquid medicament. For this, the piston rod of the drive mechanisms of such devices advances in discrete steps in a distal direction during repeated dose dispensing procedures until an end-of-content configuration has been reached, in which the piston of the cartridge reaches a distal stop or end configuration. Since the piston rod of the drive mechanism has been correspondingly and successively displaced in distal direction also the piston rod is located in a distal end-of-content position when an empty cartridge is to be replaced by a new or filled one.

For reusable injection devices it is therefore required that the drive mechanism provides a reset mechanism or reset function by way of which at least the piston rod is displaceable into an initial configuration, i.e. a zero dose configuration or zero dose position.

SUMMARY

Certain aspects of the present disclosure provide a drive mechanism of an injection device that comprises a reset function or reset mechanism allowing to at least displace a piston rod of the drive mechanism in proximal direction upon replacement of an empty cartridge. The reset function or reset mechanism should be rather robust and easy as well as intuitive to use. The reset mechanism or reset function should be implementable with a minimum number of additional components. The reset mechanism should be rather compact and space saving. Furthermore, its implementation should be smoothly integrable into the overall production and assembly process of the injection device.

In a first aspect the disclosure relates to a drive mechanism of an injection device for setting and dispensing of at least a single, preferably of multiple doses of a medicament, in particular of a liquid medicament. The drive mechanism comprises a body of a housing of the injection device. The body extends in an axial direction. Typically, it serves to directly accommodate a cartridge filled with a medicament. Alternatively, the body is connectable with a cartridge holder to accommodate the cartridge filled with the medicament.

The body of the drive mechanism typically represents and corresponds to a proximal housing component of the injection device while the cartridge holder connectable with the body represents and corresponds to a distal housing component of the injection device. Through a releasable engagement of cartridge holder and body, access to the interior of at least one of the cartridge holder and body is provided in order to replace an empty cartridge supported by the cartridge holder and/or to reset a drive mechanism located inside and supported by the body.

The drive mechanism further comprises an insert that is axially displaceable inside the housing between a proximal operating position (O) and a distal reset position (R). The insert extends across the inner diameter of the housing or spans substantially over the internal area of the housing, which may be of tubular shape. Typically, the insert is rotationally connected to the housing. In other words, the insert is rotationally fixed to the housing and cannot rotate relative to the body, with respect to a longitudinal axis extending parallel to or coinciding with the axial direction of the body. Since the insert is axially slidably displaceable inside the housing, the drive mechanism is transferable between an operating configuration and a reset configuration. Switching between operating and reset configuration is triggered and governed by the respective axial displacement of the insert relative to the body. By shifting or displacing the insert from its operating position into its reset position the drive mechanism is transferable from a conventional operating configuration or operating mode into a reset configuration or reset mode; and vice versa.

The drive mechanism further comprises a piston rod to operably engage with a piston of the cartridge. The piston rod extends in axial direction and is threadedly engaged with the insert. Typically, the insert serves as an axial guide for the piston rod. Through its threaded engagement with the piston rod, a rotation of the piston rod relative to the insert and hence relative to the housing leads to an axial displacement of the piston rod relative to the insert and relative to the housing. Especially for dispensing of a dose, wherein the piston rod advances in axial distal direction, the piston rod rotates in a dose dispensing or dose decrementing direction. Through its threaded engagement with the insert, which in operating position is axially fixed to the housing and is hence axially fixed with respect to the cartridge or cartridge holder, the piston rod induces a distally-directed displacement onto the cartridge's piston, thereby increasing a fluid pressure inside the cartridge in order to expel a predefined amount of the medicament from the cartridge.

Typically, the insert extends across and substantially fills the lateral cross-section of the interior space of the body. The insert further comprises a through opening, which may be a central through opening featuring an inner thread that is threadedly engaged with an outer thread of the piston rod.

The drive mechanism further comprises a drive sleeve rotationally coupled with the piston rod and extending in axial direction. The drive sleeve is rotationally lockable to the body for setting of a dose. The drive sleeve is also rotationally releasable from the body for dispending of a dose, respectively. By selectively locking or releasing drive sleeve and housing, hence by locking or releasing a rotation of the drive sleeve relative to the housing with regard to a rotation axis extending parallel to or matching with the axial direction the drive mechanism can be switched between a dose setting mode, in which a dose of variable size is settable or adjustable by a user of the injection device and a dose dispensing mode, in which a previously set dose is axially dispensed from the cartridge through the action of the drive mechanism.

Typically, the drive sleeve is permanently rotationally coupled or rotationally engaged with the piston rod. In the present context, rotationally or rotatably coupled means, that a rotation of the drive sleeve transfers into a rotation of the piston rod and/or vice versa. Hence, during setting of a dose the drive sleeve permanently rotationally coupled with the piston rod is hindered to rotate. During dose setting, the piston rod is therefore fixed or immobilized to prevent uncontrolled or premature dispensing of the medicament. When the insert is in operating position it is only during dose dispensing that the drive sleeve is free to rotate in order to induce and to transfer a driving torque to the piston rod for driving and advancing the same in distal direction for the purpose of dispensing of a predefined amount, hence a dose of the medicament from the cartridge.

In order to implement a reset mechanism or reset function the drive sleeve is axially displaceable relative to the body from a proximal operating position (O) into a distal reset position (R) through an axial connection of insert and drive sleeve. When in distal reset position (R), the drive sleeve is rotationally released from the body and is hence free to rotate relative to the body. Since drive sleeve and insert are axially connected, at least a distally-directed displacement of the insert from its proximal operating position towards and into its distal reset position is transferred, in particular equally transferred, to the drive sleeve. Correspondingly, insert and drive sleeve are axially coupled and are both axially displaceable between respective proximal operating positions and distal reset positions. Through the axial displacement of the drive sleeve relative to the body, which may be triggered and governed by the insert, the drive sleeve is rotationally releasable from the body, irrespective on whether the drive mechanism is in dose setting or dose dispensing mode. Through the axial connection or axial coupling of insert and drive sleeve the drive sleeve is rotationally releasable from the body even when the drive mechanism is in dose setting configuration. In this way, the reset mechanism or reset function may overrule or override the rotational lock of the drive mechanism when in dose setting mode.

Typically, the drive sleeve is of hollow tubular shape and the piston rod axially extends therethrough. The rotational coupling of drive sleeve and piston rod is obtained through at least one or several longitudinally or axially extending grooves in the outer thread of the piston rod that engage with at least one radially inwardly extending protrusion of the drive sleeve, extending from an interior sidewall portion thereof. In this way, a rotation of the drive sleeve is unalterably transferable into a respective rotation of the piston rod and vice versa. The longitudinal grooves may extend deeper into the piston rod than the structure of the thread.

When the arrangement of drive sleeve and insert is located in distal reset position the drive sleeve is free to rotate relative to the insert as well as relative to the body. The threaded engagement of insert and piston rod is typically selected and configured such, that application of a proximally-directed pressure to a distal end of the piston rod leads to a rotation of the piston rod relative to the insert and hence relative to the body. The pitch or slope of the threaded engagement of piston rod and insert is selected and designed such, that a purely proximally-directed pressure applied to the piston rod, e.g. via a pressure piece, smoothly transfers into a rotative movement thereof while the threaded insert is rotationally fixed to the body of the drive mechanism.

In addition, the materials of insert and piston rod as well as the threaded portions thereof exhibit friction coefficients that enable and support a transfer of an axially-directed pressure into a driving torque of the piston rod and hence of the drive sleeve.

In order to induce and to trigger a switching of the drive mechanism from its operating mode into the reset mode it is only necessary to displace the insert in axial direction. Such a displacement is automatically or inherently implementable through the mutual mechanical interaction of the body with a cartridge holder or with a cartridge as will be explained in more detail below.

According to a further embodiment the drive sleeve is rotatable relative to the insert. The axial coupling of drive sleeve and insert is therefore rotation invariant and independent of the rotational position of the drive sleeve with respect to the insert. In order to achieve an axial coupling of drive sleeve and insert while drive sleeve and insert are and remain rotationally disengaged and rotationally decoupled, at least one of drive sleeve and insert may comprise an annular groove or an annular protrusion extending in radial inward or radial outward direction that engages with a correspondingly-shaped groove or protrusion of the other one of drive sleeve and insert.

Typically, the drive sleeve is located proximal relative to the insert. It may axially abut with the insert, in particular with its shaft-like portion forming a threaded-through opening to engage with the piston rod. Alternatively it is also conceivable, that drive sleeve and insert are located at an axial distance. Then, at least some coupling portion of either insert or drive sleeve should be axially connected to the other one of drive sleeve and insert in order to provide the required axial coupling of drive sleeve and insert. In one embodiment the drive sleeve may comprise an annular groove near its distal end that engages with a proximally extending snap feature of the insert extending radially-inwardly into said groove.

Typically, the drive sleeve is permanently rotatable relative to the insert. In other words, the drive sleeve is permanently rotationally released from the insert. In this way, the drive sleeve is free to rotate during dose dispensing as well as during a reset operation.

In a further embodiment the insert is axially slidably arranged inside the body in proximal direction against the action of a reset spring. This means, that the insert is axially slidably displaceable in distal direction under the action of the reset spring. By means of the reset spring, the insert is hence axially displaceable from its proximal operating position into its distal reset position. In this way a quasi-automatic displacement of the insert into the reset position can be obtained as soon as an axial fixing of the insert inside the body is released or abrogated. A sliding displacement of the insert in distal direction may be triggered and released through the interaction with a cartridge holder or cartridge, typically in the course of an empty cartridge replacement.

The reset spring may comprise a helical spring. It may be arranged axially between a support structure of the body and a proximal end of the insert. With such an embodiment the reset spring comprises a compression spring that is axially compressible between a portion of the body and the insert and which serves to increase the axial distance between the body's support structure and the insert as soon as the insert is free to slide in distal direction relative to the body.

According to another embodiment the drive mechanism further comprises a lock member radially arranged between the drive sleeve and the body. The lock member is rotationally locked to the housing. The lock member may be of annular shape and may comprise an inner diameter that is configured to receive the drive sleeve and which lock member is further configured to be axially intersected by the drive sleeve. The lock member is permanently rotationally locked to the body. Hence, the lock member is impeded to rotate relative to the body with regard to the longitudinal axis of the drive mechanism. By means of the lock member the drive sleeve is selectively rotationally engageable and rotationally releasable to and from the body.

Further, by means of the lock member, a rotational coupling and a rotational release between drive sleeve and body can be attained without an axial displacement of the drive sleeve relative to the body. In other words, the drive mechanism is transferable between a dose setting mode and a dose dispensing mode exclusively through the lock member's interaction and the lock member's axial displacement with regard to the housing and/or with regard to the drive sleeve. As long as in operating mode the drive sleeve is axially fixed to the body through its axial coupling with the insert.

In order to provide a rotational interlock between lock member and body at least one of lock member and body comprises longitudinally or axially extending grooves or protrusions while the other one of lock member and body comprises correspondingly shaped protrusions or grooves that mutually engage. In this way a kind of splined engagement between body and lock member can be provided. For instance, the inside-facing sidewall portion of the body may comprise at least one axially extending slit or groove that receives a radially-outwardly extending protrusion of the lock member. In this way, a rotational interlock of lock member and body is directly attainable.

In a further embodiment the lock member is axially displaceable relative to the body between a proximal dose setting position and a distal dose dispensing position. The lock member is axially slidably disposed inside the body to selectively engage or to disengage with the drive sleeve. When lock member and drive sleeve mutually engage, the drive sleeve is rotationally locked to the body via the lock member. If drive sleeve and lock member are disengaged, the drive sleeve is rotationally released from the body, respectively. By means of a sliding displacement of the lock member relative to the body and hence relative to the drive sleeve, the drive sleeve is selectively rotationally engageable with the body and is further rotationally releasable from the body. In this way, switching of the drive mechanism between dose dispensing and dose setting mode is governed by a respective axial displacement of the lock member between its proximal dose setting position and its distal dose dispensing position. The axial displacement of the lock member is governed and triggered by at least some other component of the drive mechanism, typically by a dial sleeve, which is in axial abutment or which is axially connected to the lock member. The dial sleeve typically extends towards the proximal end of the body so that a user may directly or indirectly induce a distally-directed displacement of the dial sleeve and hence of the lock member from its proximal dose setting position into its distal dose dispensing position for initiating the dispensing of a dose of the medicament.

According to a further embodiment the drive sleeve is rotationally engaged with the lock member when the drive sleeve is in proximal operating position and when the lock member is in proximal dose setting position. During conventional use of the drive mechanism, i.e. when the drive sleeve is in proximal operating position the drive sleeve is rotationally engaged with the lock member and is hence hindered to rotate relative to the body when the lock member is in its proximal dose setting position. Displacement of the lock member into its distal dose dispensing position releases the mutual rotational interlock of lock member and drive sleeve, thereby allowing the drive sleeve to rotate in a dose dispensing or dose decrementing direction in order to apply a respective driving torque to the piston rod.

Moreover, and according to another embodiment the drive sleeve is rotationally released from the lock member when the drive sleeve is in proximal operating position and when the lock member is in distal dose dispensing position. In this way, a selective and alternating rotational engagement of drive sleeve and body is exclusively obtainable through the axial displacement of the lock member while the drive sleeve remains in its axial operating position for both dose setting and dose dispensing.

According to another embodiment the lock member is of annular shape and comprises an annular detent structure at an inward-facing sidewall portion. The detent structure of the lock member is engageable with a first annular detent structure on the outer circumference of the drive sleeve axially extending through the lock member. The first annular detent structure of the drive sleeve and the lock member's inward-facing annular detent structure are only in mutual engagement when the lock member is in proximal dose setting position and when the drive sleeve is in proximal operating position. Either a displacement of the lock member from its proximal dose setting position into its distal dose dispensing position or a displacement of the drive sleeve from its proximal operating position into its distal reset position leads to a disengagement of mutually corresponding detent structures of lock member and drive sleeve. The mutually corresponding detent structures of lock member and drive sleeve may comprise longitudinally or axially extending protrusions and/or grooves, e.g. to establish a splined engagement of lock member and drive sleeve. Alternatively, the detent structures may comprise toothed or geared structures that are equally operable and designed to provide a rotational coupling and to withstand and to counteract a driving force or driving torque of e.g. the drive sleeve.

The detent structures of the lock member and the drive sleeve are located at particular axial positions of lock member and drive sleeve so that a mutual engagement and mutual disengagement thereof is attainable at selected axial positions of lock member and drive sleeve.

In a further embodiment the lock member is axially displaceable relative to the body in distal direction against the action of a dispensing spring. In this way, an axial displacement of the lock member from its distal dose dispensing position (D) towards and into its proximal dose setting position (S) is governed or is at least supported by the dispensing spring. In this way, the drive mechanism, per default, is switchable into the dose setting mode. By way of the dispensing spring acting against or axially engaged with the lock member the drive mechanism is switchable from the dose setting mode into the dose dispensing mode only when a respective dispensing force acts against the action of the dispensing spring, e.g. when a user-induced and axially-directed dispensing force actually serves to compress the dispensing spring so that the lock member is displaced into its distal dose dispensing position.

In a further embodiment a distal end of the dispensing spring is supported by or is connected with the insert. A proximal end of the dispensing spring is then supported by or is connected with the lock member. The lock member is typically located proximally from the insert. Axially between the insert and the lock member the dispensing spring is located. The dispensing spring may be axially and distally supported by a radially-inwardly facing flange portion of the insert extending radially between an outer circumference of the insert and the central through opening of the insert.

In other words, the insert may feature or provide a cup-shaped receptacle for the dispensing spring, which receptacle is accessible from the proximal end of the drive mechanism. In this way, the dispensing spring is insertable into the insert until its distal end axially abuts against a proximally-facing support structure, e.g. against a bottom of the cup-shaped receptacle of the insert. Typically, the dispensing spring is of helical shape and comprises a compression spring that is axially compressible against the relaxing motion of the corresponding spring.

The radial diameter of the dispensing spring typically matches and corresponds to the radial diameter of the sleeve-shaped lock member. In this way, a distal end face of the lock member may almost entirely engage or abut with the dispensing spring. In this way a smooth axial sliding displacement of the lock member governed by the dispensing spring can be obtained.

According to another embodiment of the drive mechanism the insert is axially fixable inside the body by means of an axial abutment with a cartridge or by means of an axial abutment with a cartridge holder, wherein the cartridge holder serves to accommodate the cartridge. Furthermore, the insert is axially fixable in its proximal operating position by means of a fastening structure of cartridge holder or cartridge to engage with a corresponding fastening structure of the body. If the cartridge is contained and received in the cartridge holder, the cartridge holder with a proximal end is releasably connectable to a distal end of the body.

Typically, the body comprises a receptacle accessible from the distal direction to receive a correspondingly-shaped insert portion of the cartridge holder. In a radially-overlapping configuration of cartridge holder and body, mutually corresponding fastening structures of cartridge holder and body releasably engage so as to axially fix the cartridge holder to the body. Mutually corresponding fastening structures of cartridge holder and body may comprise a threaded engagement or a snap-fit engagement or similar positively or frictionally engaging fixing means.

Typically, a proximally-facing abutment portion, such as a proximal end of cartridge holder or cartridge axially abuts with the insert when cartridge holder and body are mutually assembled and connected. Due to this axial abutment the cartridge holder or cartridge actually applies a proximally-directed pressure to, e.g. a distal end face of the insert, thereby pushing the insert in proximal direction into its operating position. The force exerted by cartridge holder or cartridge in proximal direction onto the insert is typically larger than the force exerted by the reset spring so that the reset spring is compressed during mutual assembly of cartridge holder and body.

Upon release of cartridge holder and body, which comes along with a distally-directed displacement of cartridge and/or cartridge holder relative to the body, the reset spring may relax or extend and may therefore push the insert in distal direction towards and into the reset position.

By way of the axial abutment of cartridge holder or cartridge with the insert and by means of the reset spring, a quasi-automated axial displacement of the insert between its proximal operating position and its distal reset position can be implemented. In this way, a release of the cartridge holder from the body automatically transfers the drive mechanism into a reset mode, in which the piston rod, typically distally extending from the insert to a large extent, is displaceable relative to the insert and hence relative to the body back in proximal direction until an initial configuration of the drive mechanism is obtained.

In a further embodiment the drive mechanism also comprises a dial sleeve that is rotationally supported inside the body in a dose incrementing direction against the action of a drive spring. The dial sleeve is axially displaceable relative to the body between a distal dose dispensing position (D) and proximal dose setting position (S). The dial sleeve is rotationally coupled with one end of the drive spring while an opposite end of the drive spring is coupled or connected to the body or to the insert. The drive spring is typically implemented as a helical spring. It is biased through a relative rotation of one of its ends relative to the other end. In this way, the drive spring may store mechanical energy during a dose incrementing rotation of the dial sleeve relative to the body.

The stored mechanical energy of the drive spring is releaseable during a subsequent dose dispensing procedure. The drive spring is operable to induce a driving torque to the dial sleeve in a dose decrementing or dose dispensing direction, thereby also inducing a driving torque to the drive sleeve for advancing the piston rod and for dispensing of a dose of the medicament from the cartridge. In this way, the drive mechanism provides an automated dispensing, wherein a driving torque or driving force for advancing the piston rod in distal direction is at least supported or is entirely provided by the drive spring. The drive spring may be pre-tensed to a certain degree already during initial assembly of the drive mechanism.

The dial sleeve is selectively rotationally engageable with the drive sleeve. When in dose dispensing position, the dial sleeve is rotationally connected and rotationally coupled to the drive sleeve. In this way, a dispensing torque emanating from the relaxing drive spring is transferred to the dial sleeve and hence to the drive sleeve so that a distally-directed driving motion is transferred to the piston rod. When the drive mechanism is in dose setting mode, the dial sleeve is operably disconnected from the drive sleeve. In this way, during dose setting the drive spring may be further biased or tensed so that it relaxes in a subsequent dose dispensing procedure, in which the previously stored mechanical energy can be released and transferred into a respective dose dispensing rotation of the drive sleeve.

According to another embodiment the dial sleeve is in axial abutment with the lock member to displace the lock member from the dose setting position into the dose dispensing position. Typically, a distal end of the dial sleeve axially abuts with a proximal end of the lock member. For this, dial sleeve and lock member may comprise substantially equal diameters. Since the lock member is permanently rotationally locked to the insert and hence to the housing, mutually engaging contact surfaces of dial sleeve and lock member are evenly-shaped in order to provide a smooth rotation of the dial sleeve relative to the lock member. Since the lock member, typically with its distal end section, is in axial abutment with the dispensing spring, the displacement of the arrangement of dial sleeve and lock member in distal direction is conductible against the action of the dispensing spring.

In this way, inducing of a dispensing action or triggering of a dispensing action only requires to displace the dial sleeve together with the lock member in distal direction against the action of the dispensing spring. Axially releasing the dial sleeve leads to an automated proximally-directed displacement of the dial sleeve through the axial abutment with the lock member and due to the relaxing axial motion of the dispensing spring. Axial displacement of the dial sleeve from the dose setting position towards the dose dispensing position also comes along with a rotational coupling and engagement of dial sleeve and drive sleeve. During the distally-directed displacement of the dial sleeve, the dial sleeve at some stage rotationally locks or rotationally engages with the drive sleeve.

When this mutual rotational engagement of dial sleeve and drive sleeve is established, the drive sleeve is still hindered through the engagement with the lock member from rotating relative to the lock member and hence relative to the insert or body. It is only due to a further distally-directed displacement of dial sleeve together with the lock member, that the drive sleeve is rotationally released from the lock member so that the dial sleeve, still rotationally coupled with the drive sleeve may start to rotate in dose decrementing direction to transfer a respective driving torque to the drive sleeve.

According to a further embodiment the dial sleeve is rotationally engaged with the drive sleeve when the dial sleeve and hence the lock member is or are in distal dispensing position and when the drive sleeve is in its proximal operating position. Furthermore, the drive sleeve is rotationally released from the dial sleeve when the dial sleeve is in proximal dose setting position or when the drive sleeve is in proximal reset position. When the drive sleeve is in proximal reset position, it is decoupled from the dial sleeve in any axial position of the dial sleeve. Typically and per default, the dial sleeve is kept in its proximal dose setting position by means of the dispensing spring. In this default configuration, the dial sleeve is rotationally locked to the body unless a dose setting member is rotated in a dose incrementing or dose decrementing direction for setting of a dose.

Since in reset position of the insert and hence in reset position of the drive sleeve the drive sleeve is rotationally released from both, the body and the dial sleeve, the drive sleeve is rotatable towards an initial configuration and through the proximally-directed displacement of the piston rod, which proximally directed motion may be induced by a piston of a filled or new cartridge located in the cartridge holder during mutual assembly of cartridge holder and body.

According to another aspect the disclosure also relates to an injection device, typically to a pen-injector that is applicable to dispense a dose of a medicament, typically to set a dose of variable size and to dispense the previously set dose. The injection device comprises a drive mechanism as described above and a cartridge at least partially filled with the medicament. The cartridge is arranged in the body of the drive mechanism or the cartridge is arranged and fitted in a cartridge holder connectable or connected to the body of the drive mechanism. Body and cartridge holder typically form a housing of the injection device.

The injection device is particularly implemented as a so called auto-injector having an energy storage, such like a drive spring, by way of which a driving or dispensing force or torque can be provided for the injection of a dose of a medicament.

In the present context, the distal direction points in the direction of the dispensing end of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LsyB28ProB29 human insulin; B28-N-palmitoyl-LysB28ProB29 human insulin; B30-N-myristoyl-ThrB29LysB30 human insulin; B30-N-palmitoyl-ThrB39LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and µ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while µ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains µ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE DRAWINGS

In the following, an embodiment of the display arrangement, the drive mechanism and the injection device is described in detail by making reference to the drawings, in which.

DETAILED DESCRIPTION

Figure 1:
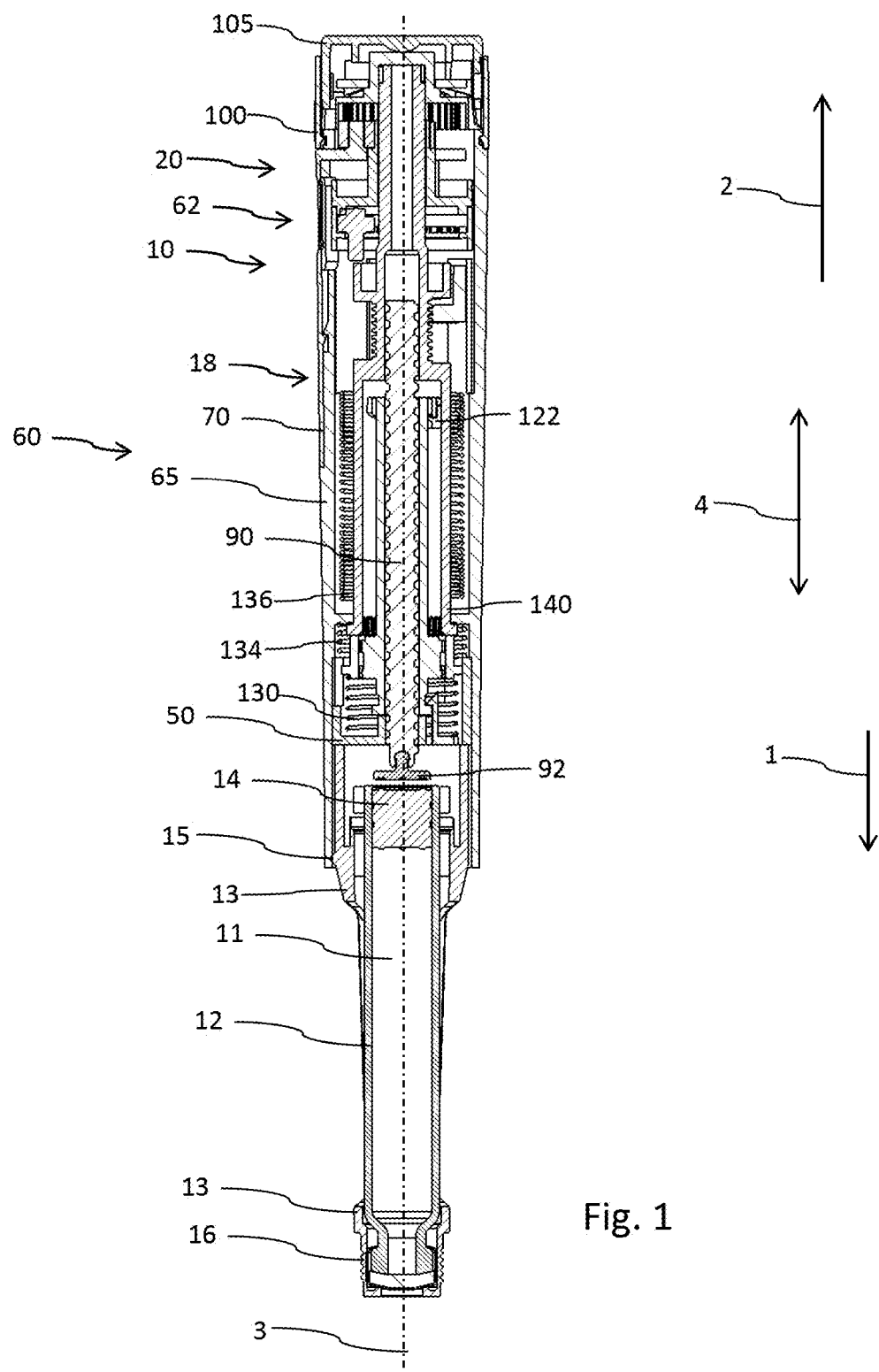
FIG. 1 shows a longitudinal cross-section through the injection device.
Figure 2:
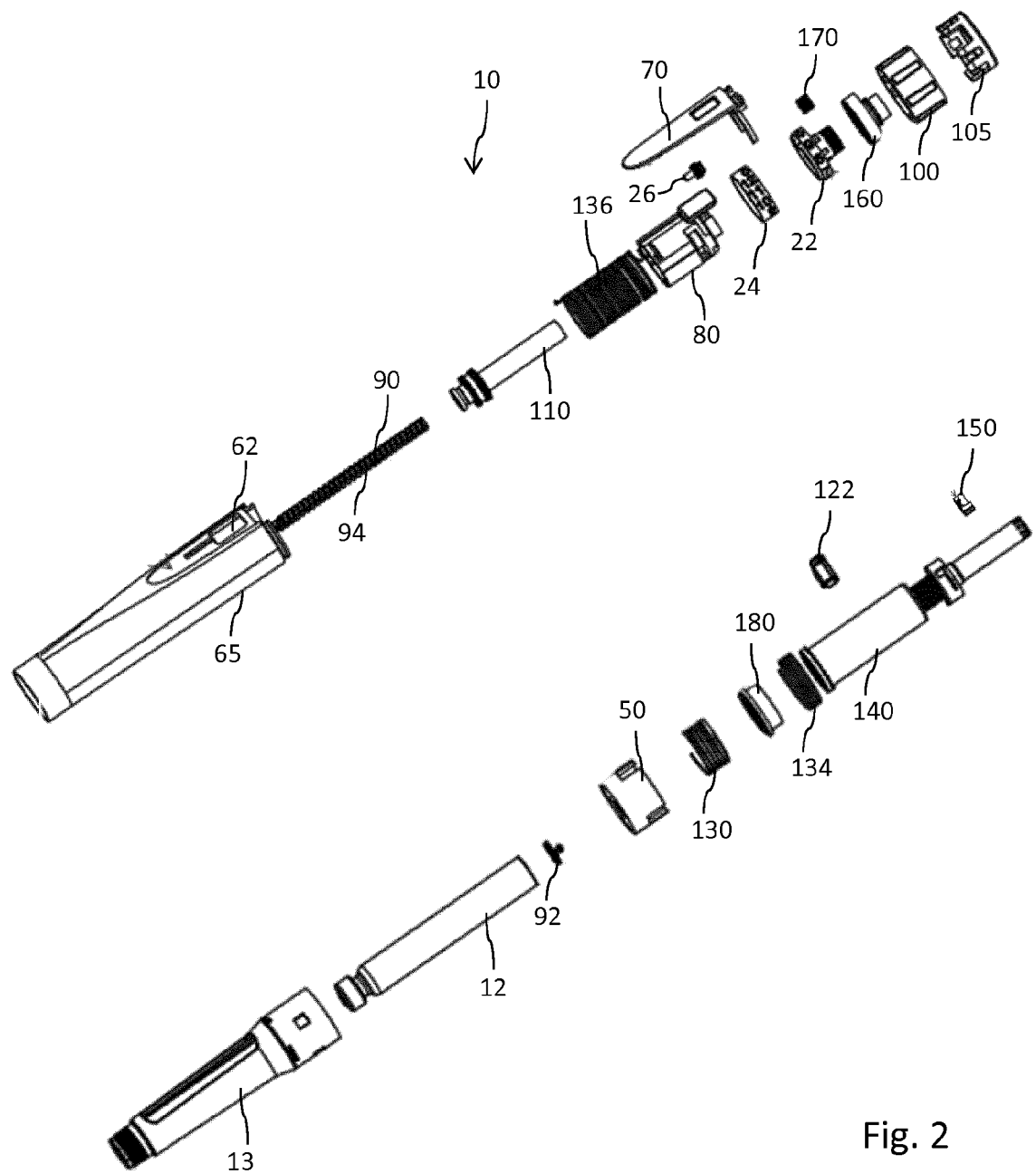
FIG. 2 shows an exploded and perspective view of the various components of the injection device.

In FIGS. 1 and 2, the complete injection device 10 is illustrated in a longitudinal cross section and in an exploded view with its various components. The injection device 10 is of pen-injector type and comprises a substantially cylindrical and axially elongated shape. In the Figures the axial distal direction is denoted with reference number 1 and the opposite proximal direction is denoted with reference number 2. The injection device 10 comprises a drive mechanism 18 and further has a housing 60, which in the present embodiment comprises a proximal body 65 and distally located cartridge holder 13 releasably attachable to the body 65. The drive mechanism 18 is located in the body 65 while the cartridge holder 13 serves to accommodate a cartridge 12 containing a medicament 11. The housing 60 defines a longitudinal or axial direction 4 and further has at its center a rotation axis 3, with regard to which various components of the injection device 10 are rotationally supported inside the housing 60.

The distal end of the body 65 is connected with a proximal end of the cartridge holder 13. The cartridge 12 typically comprises a vitreous barrel of cylindrical or tubular shape and is sealed in distal direction 1 by a pierceable sealing member, such as a septum.

In proximal direction 2, the cartridge 12 is sealed by means of a piston 14 slidably arranged in the barrel of the cartridge 12. The piston 14 typically comprises an elastomeric material, by way of which the proximal end of the cartridge 12 can be effectively sealed in a fluid- and gas-tight manner. The piston 14 of the cartridge 12 is to be operably engaged with a distal end of a piston rod 90 of the injection device's 10 drive mechanism 18. A distally directed displacement of the piston 14 typically induced and governed by the piston rod 90 leads to a respective build-up of a fluid pressure inside the cartridge 12. When the distal outlet of the cartridge 12 is connected with e.g. a needle assembly, which is not illustrated here, a predefined amount of the liquid medicament 11, which equals a previously set dose, can be expelled from the cartridge 12 and can be dispensed via the injection needle. At its distal end the injection device 10, hence the cartridge holder 13 thereof comprises a threaded socket 16 to releasably engage with the needle assembly.

The cartridge holder 13 and hence the cartridge 12 assembled therein is to be protected and covered by a removable protective cap, which is not illustrated. Prior to setting and/or dispensing of a dose, the protective cap of the injection device 10 as well as an inner needle cap of the needle assembly have to be removed. After dispensing or injecting of the medicament 11, e.g. into biological tissue, the needle assembly is typically to be disconnected from the cartridge holder 13 and is to be discarded.

The drive mechanism 18 as illustrated in the various FIGS. 1 to 16 comprises numerous functional and mechanically inter-engaging components by way of which a dose of variable size can be set and subsequently dispensed. The drive mechanism 18 is of semi-automated type. It comprises a means for storing mechanical energy during a dose setting procedure. Said mechanical energy is then usable for driving the piston rod 90 in distal direction 1 during a dose dispensing procedure. Consequently, it is the device 10 and the drive mechanism 18 that provide mechanical energy and a driving force or driving torque to conduct an injection procedure. Consequently, an injection force does not have to be provided by the user during the dose dispensing process.

Figure 6:
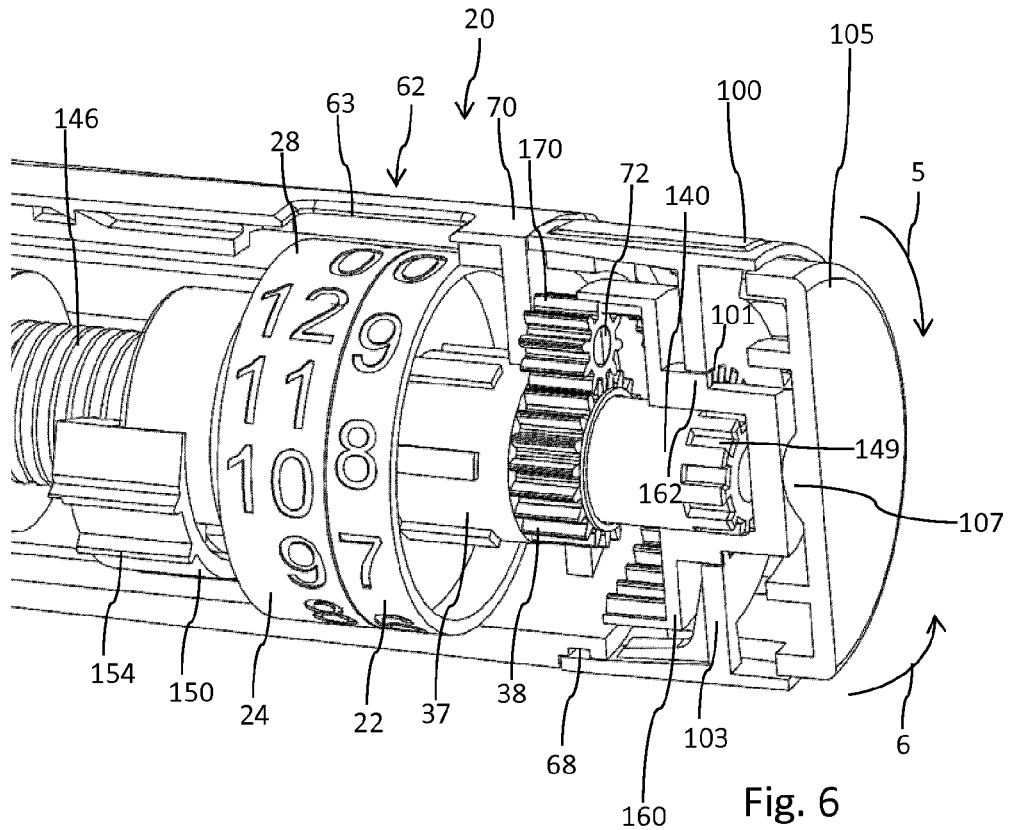
FIG. 6 shows an enlarged view of a dose display arrangement.

Dose dispensing requires distally directed advancing of the piston rod 90 relative to the cartridge 12, hence relative to the cartridge holder 13 and relative to the body 65. The drive mechanism 18 is operable to set a dose of arbitrary size. The size of a dose actually set is visually displayed to a user via a display arrangement 20 located in a proximal portion of the housing 60. The body 65 comprises a substantially cylindrical hollow shape. As shown in FIG. 6 it comprises a window 62 near its proximal end in which two display members 22, 24 appear that indicate the actual size of a dose.

As shown in FIGS. 1 and 2, there is provided an inlay 70 having a transparent cover 63 that overlaps with the window 62 or aperture of a sidewall portion of the body 65. The cover 63 can include a magnifying lens so that numbers or symbols of display surfaces 28 of the display arrangement 20 appear enlarged to a user.

Figure 12:
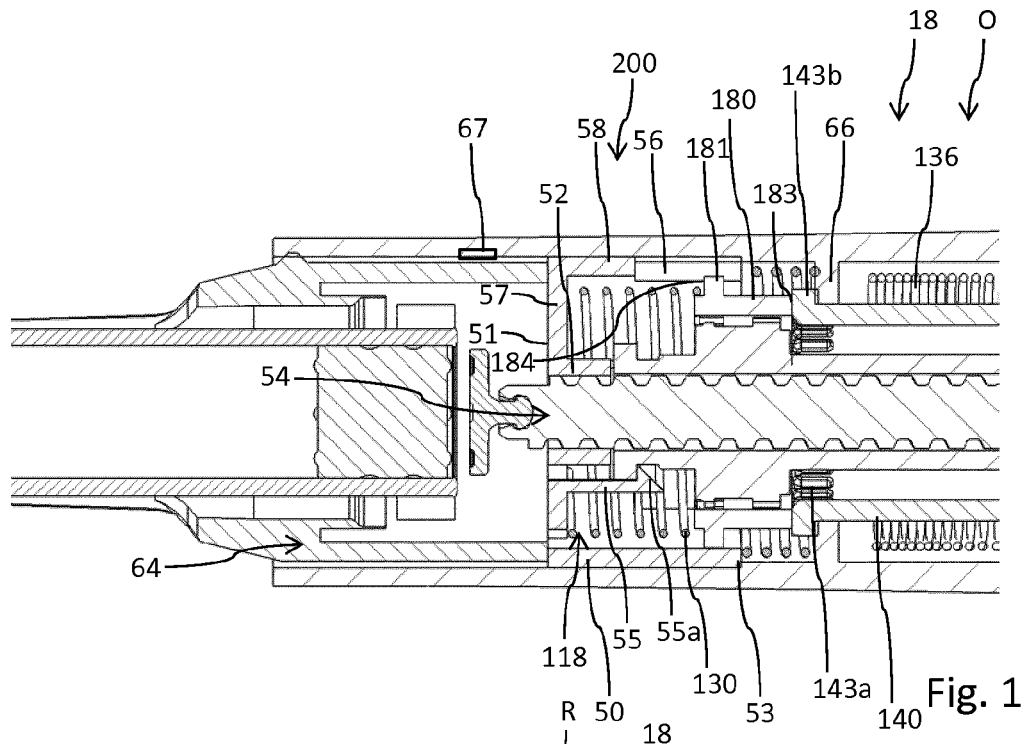
FIG. 12 is an enlarged view of the proximal portion of the drive mechanism with an insert and a drive sleeve in operation mode.
Figure 13:
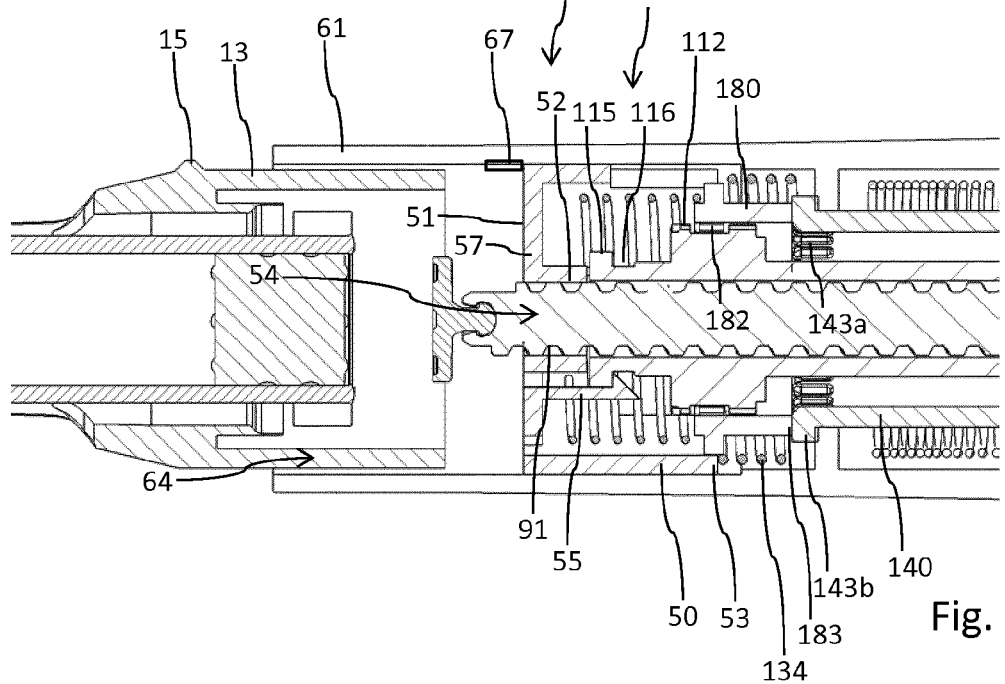
FIG. 13 shows the drive mechanism according to FIG. 12 with the insert and the drive sleeve in reset position or reset mode.
Figure 14:
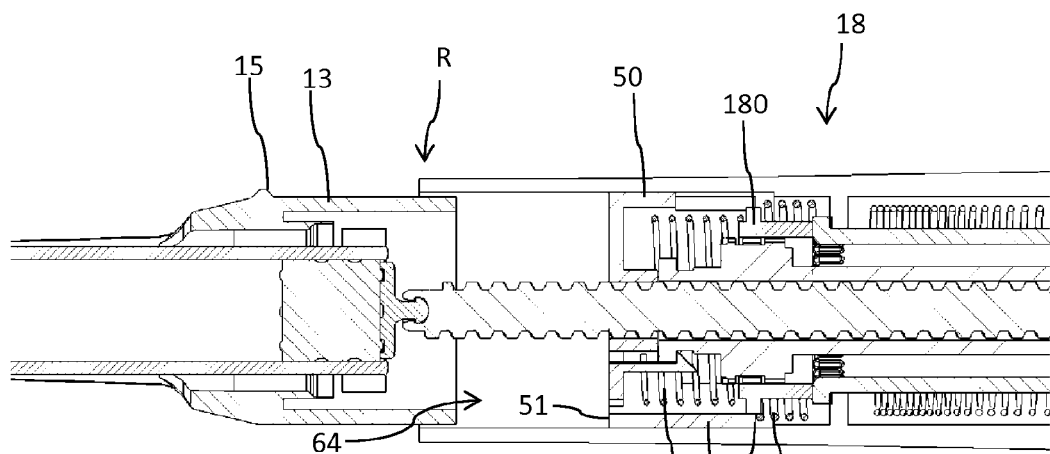
FIG. 14 shows the mutual interaction of cartridge holder and body of the drive mechanism during insertion of the cartridge holder into the body, FIG. 15 corresponds to FIG. 14 with the cartridge holder being moved further into the body.

The drive mechanism 18 comprises an insert 50 located or near a distal end of the body 65. The insert 50 is of sleeve-like shape and comprises a sidewall portion 58 of tubular shape that is rotationally locked to the body 65. The sidewall portion 58 and the body 65 comprise mutually corresponding and inter-engaging axially extending grooves and protrusions. In this way, the insert 50 is slidably disposed inside the body 65 between a proximal operating position as shown in FIG. 12 and a distal reset position as shown in FIG. 13. In other words, the insert 50 is splined to the body 65. The insert 50 further comprises a disc-shaped portion 57 at its distal end 51. The disc portion 57 extends almost completely across the inner cross-section of the body 65. Centrally located in the disc portion 57 there is provided a through opening 54 or aperture that is threaded and which is threadedly engaged with the piston rod 90. The through opening 54 is hence provided with an inner thread 52 that matches and engages with an outer thread 91 of the piston rod 90.

At its distal end the piston rod 90 is rotationally connected with a radially widened pressure piece 92, which almost completely abuts with a proximal thrust-receiving surface of the cartridge's 12 piston 14. Due to the rotatable bearing of the pressure piece 92 on the piston rod 90, the pressure piece may rest on the piston 14 while the piston rod 90 rotates during dose dispensing.

Figure 3:
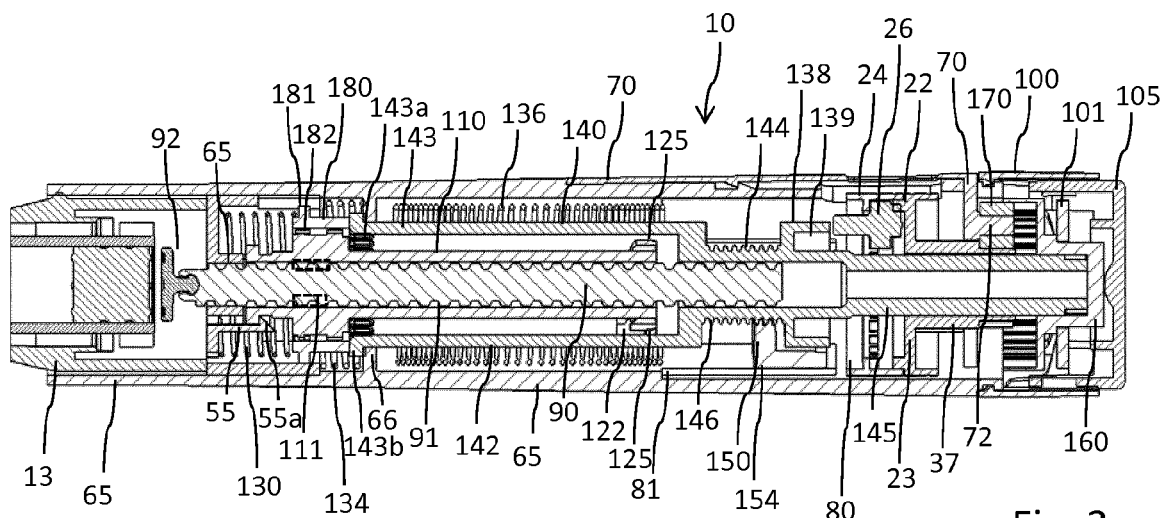
FIG. 3 shows another longitudinal cross-section through the drive mechanism in dose setting configuration.

The piston rod 90 further comprises at least one, typically at least two diametrically oppositely located longitudinal grooves 94 by way of which the piston rod 90 is in permanent rotational engagement with a drive sleeve 110. As indicated in FIG. 3 the drive sleeve 110 comprises two radially inwardly extending protrusions 111 extending in longitudinal or axial direction from its radially inwardly-facing sidewall portion. These protrusions 111 engage with the longitudinally extending grooves 94 of the piston rod 90 that are indicated in FIG. 2.

In this way the drive sleeve 110 is permanently rotationally coupled with the piston rod 90.

The drive sleeve 110 is generally axially displaceable or slidable with regard the piston rod 90. However and as explicitly shown in detail in FIGS. 12 and 13 the insert 50 and the drive sleeve 110 are axially coupled or connected by means of an axial connection 118 but are rotationally disengaged or rotationally released with respect to each other. For this purpose, the drive sleeve 110 comprises a recessed portion 116 near its distal end that is engaged with a fastening portion 55 of the insert 50. The fastening portion 55 comprises an axially extending snap member having a bevelled engaging surface 55a at its proximal end to snap-fit into the drive sleeve's recessed portion 116. Distally to the recess portion 116 the drive sleeve 110 comprises a radially widening flange portion 115 having a distal front face that is smoothly and slidably supported on a proximal front face of the insert 50, in particular of the threaded central portion of the insert 50. In this way, the insert 50 provides a smooth rotational support and axial abutment for the drive sleeve 110.

Figure 10:
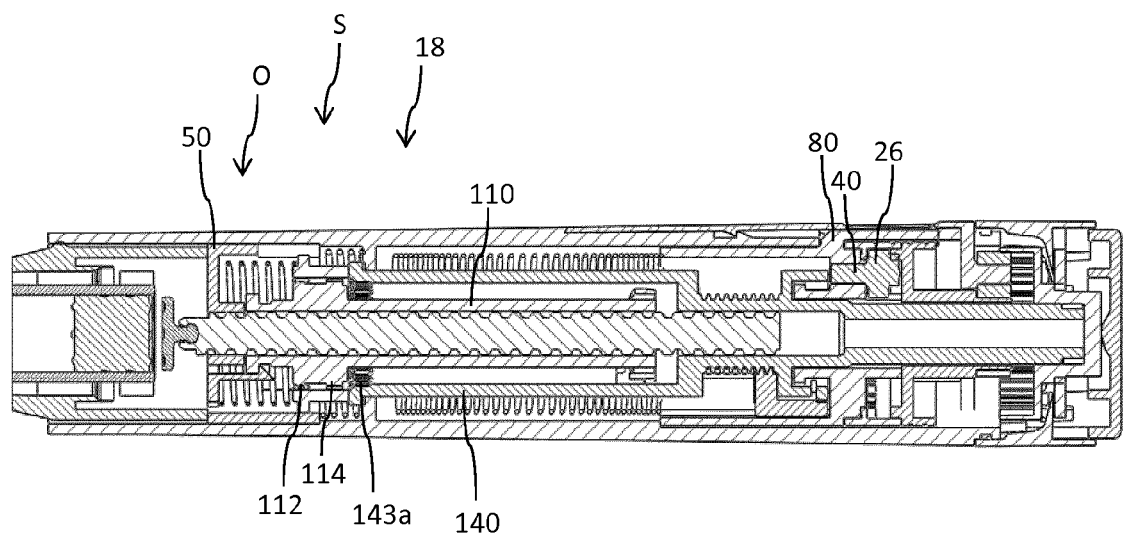
FIG. 10 is a longitudinal cross-section through the drive mechanism in dose setting mode.

As it is further apparent from FIGS. 10-13, the drive sleeve 110 further comprises a first detent structure 112 and a second detent structure 114 at its outer circumference. Here, the first detent structure 112 is located distally from the second detent structure 114. In the dose setting configuration as shown in FIGS. 10 and 12 and with the drive sleeve 110 in an operating position O the first detent structure 112 is rotationally locked and engaged with a correspondingly-shaped detent structure 182 of a lock member 180.

The lock member 180 is of sleeve-like shape and completely encompasses the outer circumference of the drive sleeve 110. The detent structure 182 is located at an inward-facing portion of the lock member 180. The detent structure 182 meshes and engages with the outward-facing first detent structure 112 of the drive sleeve 110 so long as the drive mechanism 18 is in dose setting mode. The lock member 180 is permanently rotationally locked to the body 65. For this purpose, the lock member 180 comprises at least one radially-outwardly extending protrusion 181 that engages with a longitudinally or axially extending groove at an inward-facing sidewall portion of the body 65. In this way, the lock member 180 is axially displaceable relative to the body 65 but is and remains rotationally locked thereto.

Figure 11:
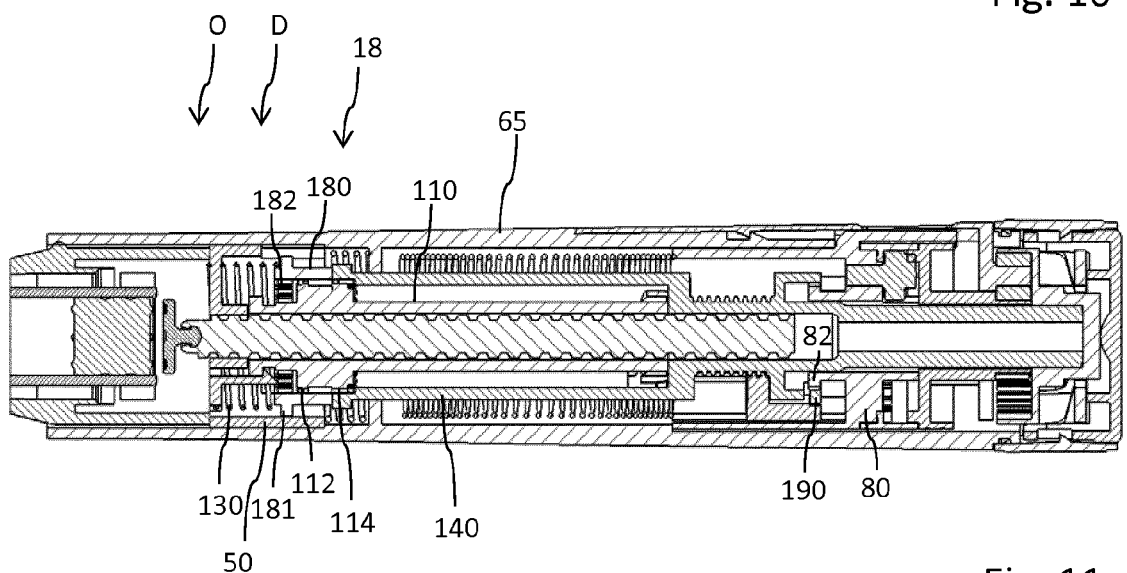
FIG. 11 is a longitudinal cross-section through the drive mechanism in dose dispensing mode.

The lock member 180 is axially displaceable between a proximal dose setting position S as shown in FIG. 10 and a distal dose dispensing position D as shown in FIG. 11. By axially displacing the lock member 180 from the dose setting position S in distal direction towards the dose dispensing position D the mutually corresponding detent structures 182 and 112 of lock member 180 and drive sleeve 110 disengage. In this way and when arriving in the dispense position as shown in FIG. 11 the drive sleeve 110 is free to rotate relative to the lock member 180 and hence relative to the body 65.

The second detent structure 114 of the drive sleeve 110 is located proximally from the first detent structure 112. It is selectively rotationally engageable with a dial sleeve 140, in particular with a distal end thereof. As it is apparent from the comparison of FIGS. 10 and 11 a detent structure 143a provided at the distal end of the dial sleeve 140 is selectively rotationally engageable with the second detent structure 114 of the drive sleeve 110 by an axial displacement of the dial sleeve 140 relative to the drive sleeve 110. The dial sleeve's detent structure 143a is provided at an inward-facing sidewall portion of the dial sleeve's 140 distal end.

Figure 5:
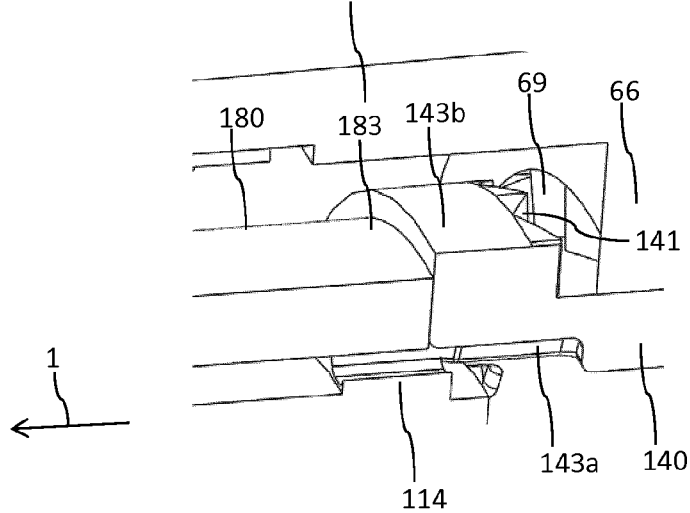
FIG. 5 shows a further enlarged perspective and partially cut view of the mutual abutment between the dial sleeve and the body.

The dial sleeve 140 further comprises a radially-outwardly extending flange portion 143b that axially abuts with a proximal end 183 of the lock member 180 as shown in detail in FIG. 5. As further shown in FIG. 12, a distal end of the lock member 180 comprises a distally-facing abutment surface 184, that is in axial abutment with a dispensing spring 130. In the present embodiment the abutment surface 184 belongs to the radially-outwardly extending protrusion 181. In this way, the protrusion 181 of the lock member 180 fulfils a double function. It serves as a lock feature to the body 65 and further axially supports the dispensing spring 130. The dispensing spring 130 is located with its distal end inside the insert 50. As shown in detail in FIG. 12, the dispensing spring 130 axially abuts with a proximal-facing side of the insert's disc portion 57. Since the insert 50 is axially fixed or axially locked relative to the body 65 when in operating mode or operating position a distally-directed displacement of the lock member 180 compresses the dispensing spring 130. In this way, distally-directed displacement of the lock member 180, which is conducted by a corresponding distally-directed displacement of the dial sleeve 140 is conducted against the restoring action of the dispensing spring 130.

Figure 4:
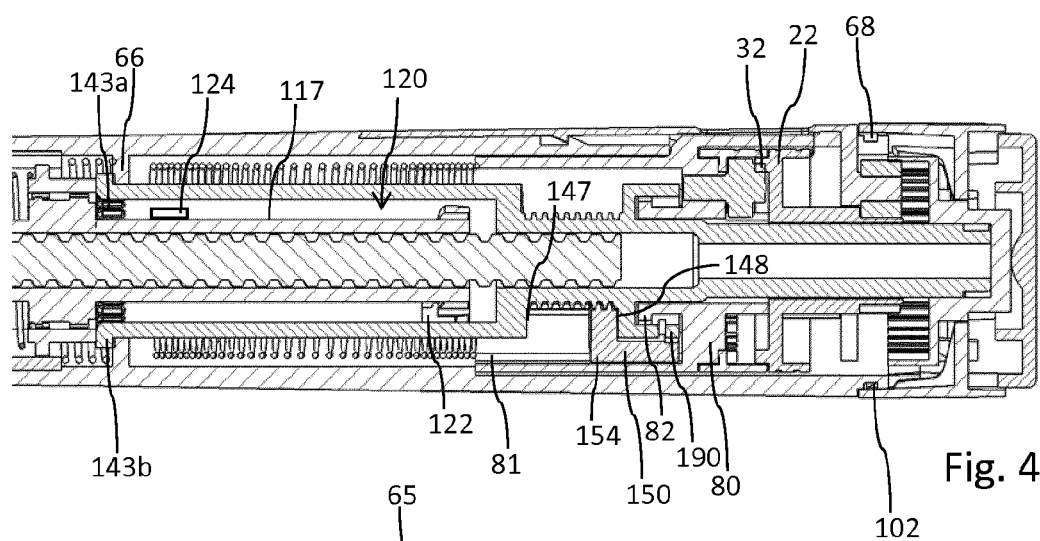
FIG. 4 shows an enlarged view of a section of the drive mechanism according to FIG. 3.

Further separated from its distal end the drive sleeve 110 comprises an outward facing threaded section 117 which in distal direction 1 is terminated by a radially outwardly and axially extending stop member 124 as shown in FIG. 4.

On the threaded section 117 there is located a last dose limiting member 122 forming a last dose limiting mechanism 120. The last dose limiting member 122 may comprise an annular or ring-like shape and has a radially inwardly-facing thread engaging with the outer threaded section 117 of the drive sleeve 110. The last dose limiting member 122 comprises two or even more radially outwardly extending protrusions 125 that extend in axial direction 4. The protrusions 125 engage with a corresponding longitudinal recess or groove 142 of the dial sleeve 140 as indicated in FIG. 3.

The dial sleeve 140 comprises a radially widened distal portion 143, a neck portion 144 proximally adjacent thereto and a proximal portion 145 extending all the way through and towards the proximal end of the housing 60 or body 65. The distal portion 143 of the dial sleeve 140 receives the drive sleeve 110 through which the piston rod 90 completely extends. A proximal portion of the piston rod 90 extending in proximal direction 2 from the proximal end of the drive sleeve 110 extends into or even through the neck portion 144 of the dial sleeve 140 as illustrated in FIG. 3.

Figure 9:
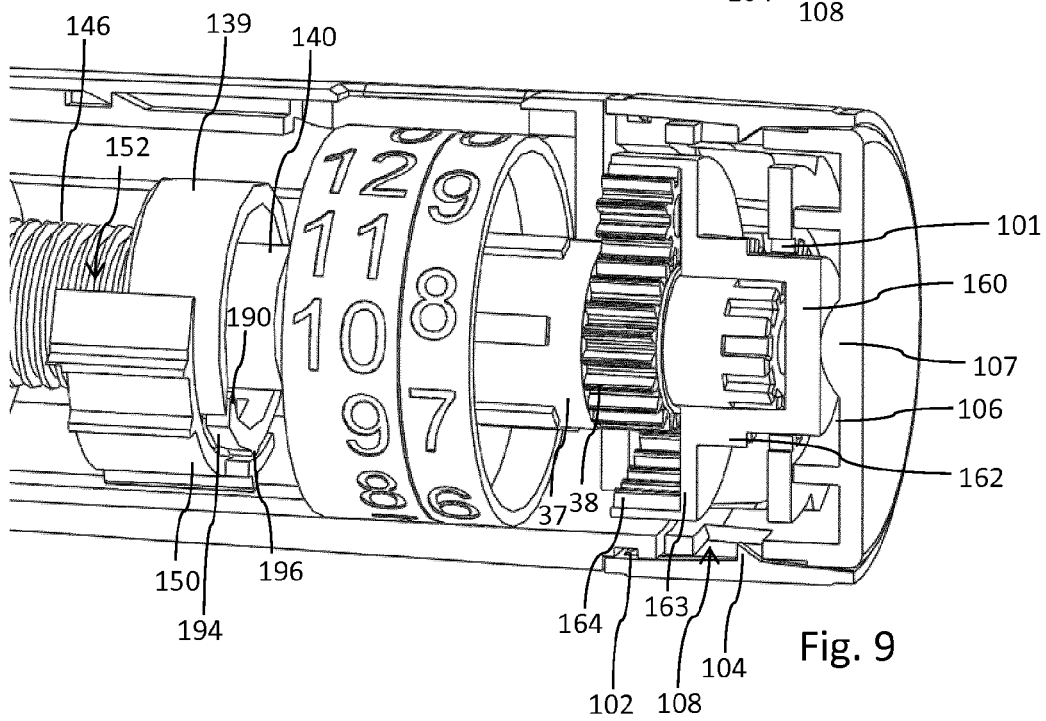
FIG. 9 shows the device according to FIG. 8 in dose dispensing mode.

In the neck portion 144 the dial sleeve 140 comprises a threaded section 146 which is threadedly engaged with a single dose limiting member 150. The single dose limiting member 150 as shown in FIG. 9 comprises a radially inwardly-facing threaded section 152 threadedly engaged with the threaded section 146 of the dial sleeve 140. Radially outwardly the single dose limiting member 150 comprises one of more radially outwardly extending protrusions 154 that are rotationally constrained but are axially guided in at least one or more corresponding a grooves 81 of an insert 80 that is permanently fixed and received in the housing 60 as indicated in FIG. 4. The grooves 81 extend in axial direction 4 so that a rotation of the dial sleeve 140 relative to the housing 60 leads to an axial displacement of the single dose limiting member 150 relative to the body 65 and/or relative to the dial sleeve 140.

The drive mechanism 18 further comprises a dose setting member 100 located at a proximal end of the housing 60. The dose setting member 100 has the form of a user-actuatable dial grip and is rotationally supported on the housing 60. As illustrated in FIGS. 6 to 9 the dose setting member 100 may even serve as a proximal extension of the body 65. Near its distal end the dose setting member 100 comprises a radially inwardly extending protrusion 102 engaging with a correspondingly-shaped recess 68 at the body's 65 proximal end. In this way, the dose setting member 100 is axially constrained and axially secured to the body 65.

Figure 8:
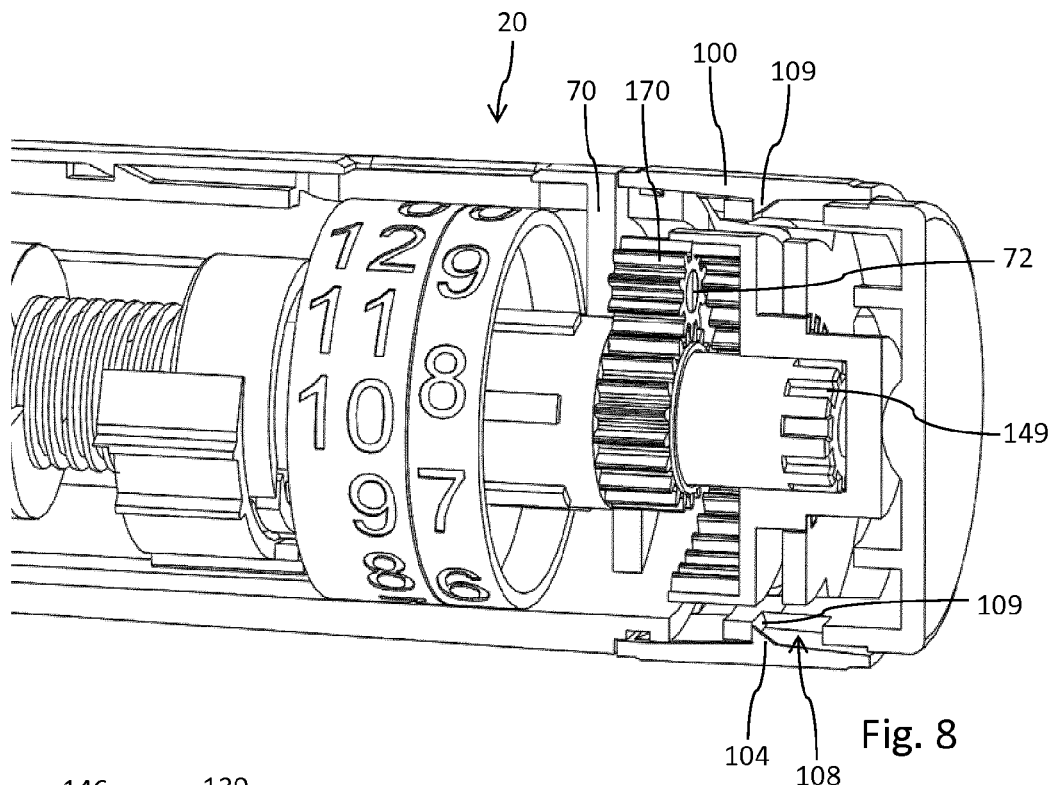
FIG. 8 shows the display arrangement and a proximal end of the drive mechanism in dose setting mode.

At the very proximal end of the injection device 10 there is provided a dose button 105. The dose button 105 is rotationally fixed to the dose setting member, e.g. by way of a splined interface, providing a rotational coupling of dose setting member 100 and dose button 105 but allows for an axial displacement of the dose button 105 relative to the dose setting member 100 and hence relative to the body 65. As shown in FIG. 9, the dose button 105 is axially slidably displaceable relative to the dose setting member 100 through a snap fit engagement provided by a radially inwardly extending protrusion 104 of the dose button 105 located in a recess 108 of the dose setting member 100. As shown in FIG. 8, the recess 108 comprises a distal stop face by way of which the dose button 105 is axially constrained with regard to the dose setting member 100 when the drive mechanism 18 is in dose setting mode S.

In a central portion of an end face 106 the dose button 105 comprises a distally-extending bulged portion 107 which is in permanent and direct abutment with a proximal end face of a ring gear 160. The ring gear 160 comprises a cup-shaped central receptacle to receive a proximal end of the dial sleeve 140. The ring gear 160 is permanently rotationally and axially connected to the dial sleeve 140, via the dial sleeve's detent structure 149 at the proximal end of the dial sleeve 140. A rotation of the ring gear 160 as well as any axial displacement of the ring gear 160 equally transfers to the dial sleeve 140.

The ring gear 160 is selectively rotationally engageable with the dose setting member 100. As indicated in FIG. 9, the ring gear 160 comprises an outwardly facing geared section 162 that is engageable with a radially inwardly extending detent structure 101 or with a correspondingly geared or toothed structure of the dose setting member 100. In this way, any rotation of the dose setting member 100 relative to the housing 60 can be equally transferred to a respective rotation of the ring gear 160. The ring gear 160 further comprises a radially-widened portion 163 at its distal end that comprises an annular geared structure 164 at an inward-facing sidewall portion.

Figure 7:
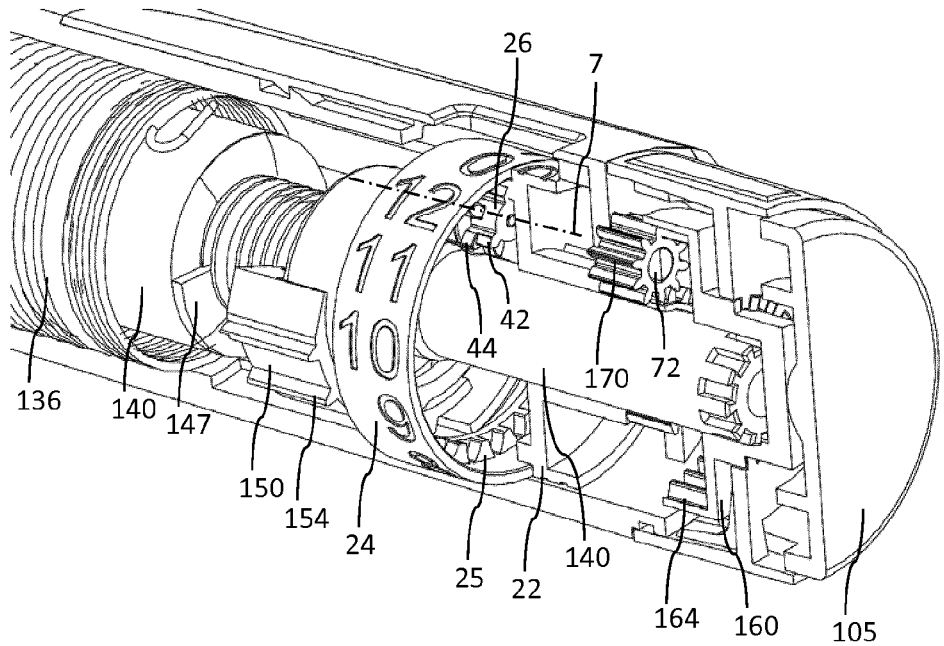
FIG. 7 shows another perspective view of the dose display arrangement.

As illustrated in FIGS. 6 and 7, the geared structure 164 of the radially widened portion 163 meshes with a planet gear 170 that is rotationally arranged on a bearing 72 of the inlay 70. Hence, the planet gear 170 is fixed to the inlay 70 and hence fixed to the body 65 but is rotatable with respect to the bearing 72 extending in axial direction 4.

The planet gear 170 further meshes with a geared section 38 of an axially-extending shaft 37 of a first display member 22 of a display arrangement 20. The display arrangement 20 comprises a first sleeve-like or annular-shaped display member 22 as well as a second sleeve shaped and annular display member 24. The second display member 24 is arranged axially adjacent to the first display member 22. First and second display members 22, 24 each comprise a display surface 28 that is provided with various consecutive symbols by way of which a two or three digit number representing the size of the dose can be illustrated in the window 62 of the body 65.

First and second display members 22, 24 are mutually coupled by means of a coupling member 26. As shown in FIG. 10, the coupling member 26 comprises an axially-extending shaft 40 that is rotationally supported in a corresponding bearing of the insert 80. In this way, the coupling member 26 is free to rotate with regard to the insert 80 and hence with regard to the body 65 but is fixed in axial direction 4. As it is apparent from FIG. 3, the proximal end of the coupling member 26 is axially constrained by a flange-like and radially outwardly extending body 23 of the first display member 22, which body 23 radially extends between the annular display surface 28 and the radially inwardly located shaft 37 of the first display member 22.

The first display member 22 is permanently rotationally engaged with the dial sleeve 140. When the dial sleeve 140 during dose setting is dialed in a dose incrementing direction 5 the first display member 22 and, depending on the size of dose and depending on the number of revolutions of the dose setting member 100, also the second display member 24 starts to rotate in order to display consecutive rising numbers in the window 62 that represent the size of the dose actually set. During a dose dispensing procedure, hence when the device 10 is in dose dispensing mode D, which is to be triggered by a distally-directed depression of the dose button 105 the dial sleeve 140 is disconnected or disengaged from the dose setting member 100. During dose dispensing the dial sleeve 140 and the drive sleeve 110 both rotate in an opposite dose decrementing direction 6 according to which the display arrangement 20 with its first and second display members 22, 24 returns into an initial configuration.

In the following setting of a dose will be described.

In an initial configuration as illustrated in FIG. 3 the dispensing spring 130 applies proximally-directed pressure to the lock member 180 and further onto the dial sleeve 140. Since the proximal end of the dial sleeve 140 is received in a receptacle of the ring gear 160, the ring gear 160 is also located in a proximal end position. Due to the axial abutment of the ring gear 160 with the dose button 105, the dose button 105 is also biased into an inactive and proximal initial position, in which the drive mechanism 18 is in dose setting mode S.

In this configuration as it is shown in an enlarged view in FIG. 6 the toothed structure 101 of the dose setting member 100 is engaged with the geared section 162 of the ring gear 160. A rotation of the dose setting member 100 in a dose incrementing direction 5 therefore leads to a respective rotation of the dial sleeve 140. As a consequence, the single dose limiting member 150 travels in axial direction, presently in distal direction 1. The dial sleeve 140 comprises a distal stop 147 as shown in FIG. 7 as well as a proximal stop 148 as indicated in FIG. 4 to engage with a respective stop feature of the single dose limiting member 150. Hence, when a maximum allowable dose is set, e.g. 120 IU of insulin, the single dose limiting member 150 has traveled all the way in distal direction 1 until it engages with its stop with a corresponding distal stop 147 of the dial sleeve 140. Mutually corresponding stops 147, 148 of the dial sleeve 140 and of the single dose limiting member 150 typically extend in axial and radial direction so that a well-defined and directly acting stop can be provided as soon as a predefined angular position of the dial sleeve 140 has been reached.

In the initial configuration of the drive mechanism 18 as shown in FIG. 4, a stop of the single dose limiting member 150 is in engagement with the zero dose stop 148 of the dial sleeve 140. In this stop configuration a rotation of the dial sleeve 140 in dose decrementing direction 6 is prevented. So in an initial dose setting configuration S of the drive mechanism 18 a dialing of the dose setting member 100 in a dose decrementing direction 6, that would lead to a negative dose size is effectively prevented. Moreover, the zero dose stop configuration also limits the dispensing procedure and serves to terminate the dispensing procedure.

The dial sleeve 140 is further coupled and connected with a helical drive spring 136 extending around the outer circumference of the dial sleeve 140. A proximal end of the helical drive spring 136 is fixed to the body 65. Typically, and in an initial configuration as shown in FIG. 3 the drive spring 136 is already rotationally pre-loaded. Upon rotation of the dial sleeve 140 in dose incrementing direction 5 the drive spring 136 is biased and wound-up further so as to increase the mechanical energy stored in the drive spring 136. In the initial or dose setting configuration S the drive sleeve 110 is engaged and rotationally locked to the body 65 via the lock member 180.

As it becomes apparent from FIGS. 4 and 5 the body 65 comprises a radially-inwardly extending flange portion 66 provided with a toothed portion 69 facing in distal direction 1. Correspondingly with the toothed portion 69 also the dial sleeve 140 comprises a radially-outwardly extending flange portion 143b that has a toothed surface or flange portion 141 facing in proximal direction 2. The teeth of the toothed portions 141 and 69 mutually mesh during a rotation of the dial sleeve 140 in dose incrementing direction 5 as well as in dose decrementing direction 6. The engagement of the toothed portions 69, 141 is designed and configured such, that an unwinding or returning torque of the biased drive spring 136 is less than a torque required to rotate the dial sleeve 140 in the opposite dose decrementing direction 6 relative to the body 65. The force or torque required to overhaul the ratchet type engagement of dial sleeve 140 and body 65 is governed and determined by the static and dynamic friction coefficients of the toothed portions, 69, 141, the geometry and the ramp angle of the mutually engaging toothed portions 69, 141 and the axial biasing or load that is applied by the dispensing spring 130.

Since the dial sleeve 140 is axially biased by the dispensing spring 130 via the lock member 180 the dial sleeve 140 shuttles back and forth due to the axial extension of the mutually engaging toothed portions 141, 69 as the dial sleeve 140 is rotated in the dose incrementing direction 5 or in dose decrementing direction 6 relative to the body 65. The mutual engagement of the toothed portions 141, 69 does not only keep the drive spring 136 biased torsionally under load does not only prevent a self-actuated release of the drive spring 136 but also provides an audible as well as a tactile feedback to the user of the device during actuation, hence during dialing of the dose setting member 100. The shape and geometry of the mutually engaging inclined crown wheel shaped tooth portions 141, 69 of dial sleeve 140 and body 65 is selected such that the dial sleeve 140 can be also rotated in a dose decrementing direction 6 in case that a selected dose should be too large.

During setting of a dose and during rotation of the dial sleeve 140 relative to the drive sleeve 110 additionally the last dose limiting member 122 advances from its initial proximally-located position in axial direction, e.g. in distal direction 1. Since the dial sleeve 140 and the drive sleeve 110 rotate in unison during a dose dispensing procedure the last dose limiting member 122 will not be subject to any further axial displacement. During subsequent dose setting procedures the last dose limiting member 122 will be displaced further in axial direction 1 until it engages with a radial and/or axial stop 124 provided at a distal end of the drive sleeve 110 as it is indicated in FIG. 4. This mutual abutment serves to prevent further dialling and the selection of a dose that would exceed the amount of medicament 11 left in the cartridge 12.

During a dose setting procedure but also during dose dispensing the ring gear 160 is permanently engaged with the dial sleeve 140 as well as with the planet gear 170. A rotation of the dial sleeve 140 in dose incrementing direction 5, e.g. induced by a user dialing the dose setting member 100 relative to the housing 60, transfers into a rotation of the first display member 22. On the outer circumference of the disc- or sleeve-shaped first display member 22 there is provided a display surface 28 on which consecutive numbers ranging from 0-9 are equidistantly located.

The first display member 22 comprises an axially extending shaft 37 in a central portion. The rather smooth and even-shaped shaft 37 is intersected by the proximal portion 145 of the dial sleeve 140. The smooth inner bore of the tubular shaft 37 forms a bearing around the dial sleeve 140. In this way, the first display member 22 is rotationally supported on the dial sleeve 140. Axially adjacent to the first display member 22 there is located the second display member 24, which comprises also numerous digits ranging from 0-12. While the first display member 22 represents the units of a two or three digit number the second display member 24 represents the tens or decades of a two or three digit number. In this way, every discrete dose size between 0-120 IU can be illustrated by the display arrangement 20. The display arrangement 20 is by no way limited to the illustration of dose sizes between 0 and 120 but may be used also for other scales and other medicaments.

The display surfaces 28 of first and second display members 22, 24 axially flush. First and second display members 22, 24 that constitute an odometer-like display arrangement 20 are coupled by means of a coupling member 26. As shown in FIG. 7, the coupling member 26 is located radially offset from the centrally-located rotational axis 3 and is rotatable relative to a coupling axis 7 extending parallel to but radially offset from the centrally-located rotation axis 3.

As indicated in FIGS. 4 and 7 the first display member 22 comprises an axially extending cam 32 near its outer edge or outer circumference. Hence, the cam 32 is located eccentric with regard to the rotation axis 3 and also with regard to the center or shaft 37 of the first display member 22. The cam 32 is configured to mesh with a first geared section 42 of the coupling member 26. The first geared section 42 comprises numerous equidistantly arranged radially outwardly extending first teeth. Every time the cam 32 reaches and passes by the coupling member 26, the cam 32 circumferentially or tangentially abuts and engages with one of the first teeth of the first geared section 42, thereby inducing a well-defined and limited rotation onto the coupling member 26.

The coupling member 26 further comprises a second geared section 44 with a number of second teeth. The second geared section 44 is located axially offset and at an axial distance from the first geared section 42. As shown in FIG. 7 the second geared section 44 meshes with a radially inwardly-facing geared section 25 of the second display member 24, which is configured as a sleeve and which is rotationally supported by the insert 80 and body 65. In this way any rotation of the coupling member 26 induced by the cam 32 of the first display member 22 is transferred into a corresponding rotation of the second display member 24 for each direction of rotation.

The planet gear 170 that rotationally couples the dose setting member 100, the ring gear 160 and finally the first display member 22 advantageously implements a gear ratio between the ring gear 160 and the first display member 22. This gear ratio allows for the dose setting member 100 to be rotated whilst providing a greater amount of rotation within the first display member 22. This has the advantage of allowing, for example, half a turn of the dose setting member 100 to advance the first display member 22 by a complete revolution. The number of user-operated rotations for setting of a high-dosage can therefore be reduced. In this way the user comfort as well as user convenience of the injection device 10 can be improved.

In the following the dispensing of a dose will be described.

For dispensing of a dose the user simply depresses the dose button 105 in distal direction 1. In this way and due to the consecutive axial abutment of dose button 105, ring gear 160 and dial sleeve 140, the dial sleeve 140 is displaced in distal direction 1 in unison with the lock member 180, which axially abuts with the dial sleeve 140. As the ring gear 160 is displaced in distal direction 1 its geared section 162 disengages from the toothed structure 101 of the dose setting member 100 as it is illustrated in FIG. 9. There, the drive mechanism 18 is illustrated with the dose button 105 depressed.

As a consequence, the ring gear 160 and hence the display arrangement 20 with its first display member 22 is decoupled from the dose setting member 100. Any further rotation of the dose setting member 100 therefore no longer has an influence on the angular position of the dial sleeve 140. With the dose button 105 at least partially depressed as illustrated in FIG. 11 a further manipulation of the dose size is prevented. Moreover, the display arrangement 20 which remains engaged with the ring gear 160 is decoupled from the dose setting member 100. In a partially depressed configuration the dial sleeve 140 is displaced in distal direction 1 to such an extent that the radially inwardly-facing detent structure 143a engages with the second detent structure 114 of the drive sleeve 110. In this way dial sleeve 140 and drive sleeve 110 become rotationally locked together.

In the partially depressed configuration the drive sleeve 110, in particular its distally-located detent structure 112 is still engaged and coupled with the detent structure 182 of the lock member 180. The drive sleeve 110 is still hindered from rotating relative to the body 65 but is already rotationally engaged with the dial sleeve 140 that is drivable by the wound-up drive spring 136. In the course of fully depressing the dose button 105 in distal direction 1 the rotational coupling between the dial sleeve 140 and the drive sleeve 110 is established and activated before the drive sleeve 110 is liberated or decoupled from the lock member 180 and hence from the body 65. In this way uncontrolled slip of the drive sleeve 110 can be effectively prevented.

As the dose button 105 is completely depressed in distal direction 1 the detent structure 182 of the lock member 180 is shifted distally with regard to the first detent structure 112 of the drive sleeve 110 so as to rotationally disengage drive sleeve 110 from lock member 180. Torque and mechanical energy stored in the drive spring 136 is then transmitted through the dial sleeve 140 to the drive sleeve 110 causing it to rotate. A rotating drive sleeve 110 leads to a respective rotation of the piston rod 90, which due to its threaded engagement with the insert 50 advances in distal direction 1 to expel a predefined amount of the medicament 11 from the cartridge 12.

During the dispensing procedure the dial sleeve 140 also rotates in the dose decrementing direction 6. The single dose limiting member 150 returns towards its initial configuration as shown in FIG. 4 until it engages with a corresponding stop 148 of the dial sleeve. Simultaneously, the rotation of the ring gear 160 causes the first display member 22 to rotate back towards a zero dose position A dispensing procedure may be abruptly stopped when the user releases the dose button 105. Then, under the action of the dispensing spring 130 the lock member 180 and the drive sleeve 110 will first mutually re-engage before the dial sleeve's detent structure 143a disengages from the drive sleeve's second detent structure 114.

When the dial sleeve 140 returns into its initial proximal dose setting position S under the action of the dispensing spring 130, chamfers or beveled portions provided on a proximal end of the first detent structure 112 of the drive sleeve 110 or on detent structure 182 of the lock member 180 serve to induce a slight counter-directed rotation of the drive sleeve 110. Due to this small but distinct counter-rotation the piston rod 90 will be retracted by a predefined distance in proximal direction. This backs the pressure piece 92 away from the piston 14 of the cartridge 12 so that the piston 14 may elastically relax and decompress into an initial configuration in proximal direction 2 so that the elastic piston 14 exerts no or at least a reduced pressure on the medicament 11 contained in the cartridge 12. In this way, post dispensing droplet generation to be observed at the distal tip of the needle can be effectively reduced.

In order to provide an audible feedback during dose dispensing and in order to indicate to a user that a dispensing procedure is in progress the drive mechanism 18 and the injection device 10 comprise a clicking member 190 that audibly interacts with a toothed structure 82 of the insert 80 during dose dispensing but which is disengaged and decoupled from the toothed structure 82 when the drive mechanism 18 is in dose setting configuration. The clicking member 190 as it is shown in FIG. 9 comprises an arched shape and is provided at a proximal end of a cup-shaped and radially widened receptacle 139 on the proximal portion 145 of the dial sleeve 140. The receptacle 139, radially confined by a rim shaped side wall portion 138, opens towards the proximal end and is adapted to receive a circumferential or ring-shaped toothed structure 82 of the insert 80, which is fixed to the body 65.

The clicking member 190 and the toothed structure 82 are axially offset when the drive mechanism 18 is in dose setting mode S as shown in FIG. 4. It is due to the distally-directed displacement of the dial sleeve 140 for switching of the drive mechanism 18 in dose dispensing mode D that the clicking member 190 engages and meshes with the toothed structure 82 as it is apparent from FIG. 11. As the dial sleeve 140 rotates in dose decrementing direction 6 the clicking member 190 repeatedly contacts and slides along consecutive teeth of the insert's 80 toothed structure 82. With each successive tooth an audible click sound is generated indicating to the user that dose dispensing is still in progress.

The clicking member 190 comprises a radially inwardly extending nose portion 194 matching in shape and geometry with the shape of the saw-tooth-like shaped toothed structure 82.

As shown in FIG. 9 at a predefined tangential or circumferential distance from the free end of the clicking member 190, where the nose portion 194 is provided, the clicking member 190 comprises a radially outwardly extending protruding or bulged portion 196. The bulged portion 196 extends slightly radially outwards compared to tangentially adjacent and rather smooth and arc-shaped portions of the clicking member 190. As the end of the dispensing procedure approaches, which coincides with a returning of the single dose limiting member 150 into its proximal end position as indicated in FIG. 4, the single dose limiting member 150 engages with the bulged portion 196 and applies a radially inwardly-directed tension or pre-tension onto the clicking member 190.

In this way, the flexible length of the clicking member 190 is effectively shortened and the clicking member, and thus also its curved clicking arm are both stiffened. As a zero dose configuration is approached that coincides with a termination of the dispensing procedure a more energetic click sound is generated, thereby audibly indicating to a user that the end of the dispensing procedure has been reached.

In FIGS. 12 and 13, the principal functionality of the reset function or of a reset mechanism 200 of the drive mechanism 18 is schematically illustrated. The reset mechanism 200 is equipped with a particular reset spring 134, which is located axially between the insert 50 and the radially-inwardly-facing flange portion 66 of the body 65. The reset spring 134 comprises a helical spring and axially abuts with a distal end against the insert 50, in particular against a proximal end 53 of the insert 50. An opposite proximal end of the reset spring 134 is axially supported by the rim-shaped and radially-inwardly extending flange portion 66 of the body 65.

In the operating position O as shown in FIG. 12, the reset spring 134 is axially compressed. In the operating position O, the insert 50 is also axially fixed with regard to the body 65. As shown in FIG. 12, a proximal end of the cartridge holder 13 is in axial abutment with the distal front face of the insert 50. Moreover, the cartridge holder 13 comprises a fastening structure 15 at a sidewall portion to mate and to engage with a correspondingly-shaped fastening structure 61 of the body.

By means of mutually corresponding fastening structures 15, 61, cartridge holder 13 and body 65 are releasably engageable. In the present embodiment, the mutual engagement of cartridge holder 13 and body 65 is attainable via a snap-fit engagement, wherein the proximal insert portion of the cartridge holder 13 is inserted into a distal receptacle 64 of the body 65. Due to the fixing of the cartridge holder 13 to the body 65, the insert 50 is axially locked in place inside the body 65. The insert 50 and hence the drive sleeve 110 axially connected therewith therefore remain in operating position O as long as the cartridge holder 13 is connected to the body 65.

In FIG. 13 a reset configuration R of the drive mechanism 18 is illustrated. There, the cartridge holder 13 is disconnected and removed from the body 65. As a consequence, the insert 50 is free to be displaced in distal direction 1 under the action of the reset spring 134. As shown in FIG. 13, the insert 50 is displaceable in distal direction 1 until it engages with a reset stop 67 provided at an inward-facing sidewall portion of the body 65. Due to the axial connection 118 of insert 50 and drive sleeve 110, the drive sleeve 110 together with the piston rod 90 are displaced in distal direction 1 so that the drive sleeve's first detent structure 112 disengages from the lock member's detent structure 182 as shown in FIG. 13.

As it is further illustrated there, the lock member's detent structure 182 is located axially between first and second detent structures 112, 114 of the drive sleeve 110 but is operably disconnected from any of these two detent structures 112, 114. In this way, the drive sleeve is rotationally released and rotationally disengaged from the lock member 180. The drive sleeve 110 is hence free to rotate relative to the insert 50, the body 65 as well as relative to the dial sleeve 140.

Figure 15:
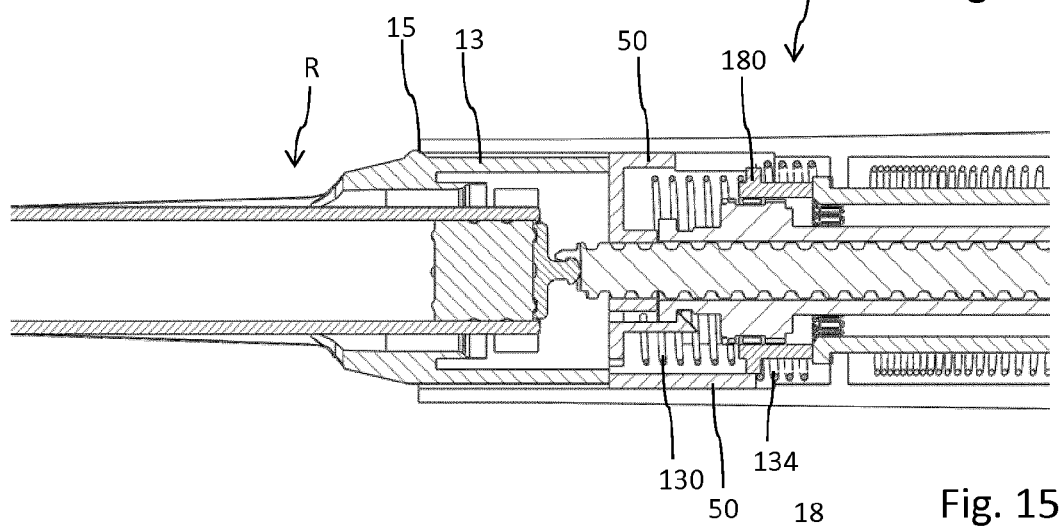
Figure 16:
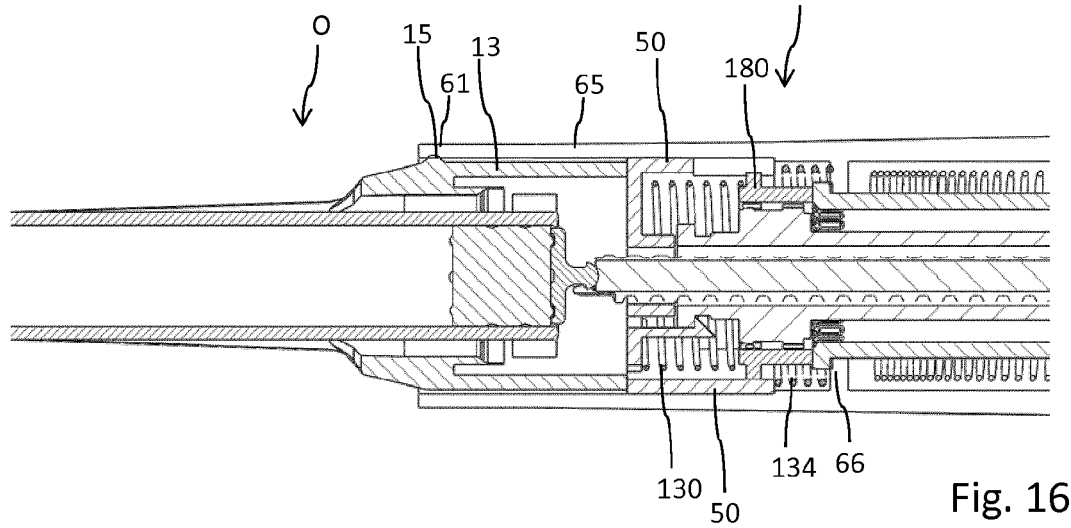
FIG. 16 shows a configuration, in which cartridge holder and body are axially fixed and connected.

Upon replacement of the cartridge 12 and during reconnection of cartridge holder 13 and body 65 the cartridge 12 in particular its piston 14 exerts a proximally-directed pressure onto the pressure piece 92. Due to the pitch and slope of the threaded engagement of piston rod 90 and insert 50, the piston rod 90 is set in a rotative motion in response to the proximally applied pressure. This rotation of the piston rod 90 leads to a corresponding rotation of the drive sleeve 110. In this way and since the dial sleeve 140 is still rotationally locked to the body 65, the last dose limiting member 122 also returns into its initial position. When a mutual abutment configuration between cartridge holder 13 and insert 50 is reached as it is illustrated in FIG. 15, a further proximally-directed displacement of the cartridge holder 13 relative to the body slidably returns the insert 50 from the reset position R into the operating position O as shown in FIG. 16.

In an alternative embodiment it is also conceivable that it is the cartridge 12 itself that axially abuts with the insert 50 to return the insert 50 from its distal reset position R into the proximal operating position O. In such an embodiment, the vitreous barrel of the cartridge 12 would be even biased in distal direction 1 by means of the insert 50 and the reset spring 134. This could lead to the benefit of providing a distally-directed biasing force onto the cartridge 12, thereby maintaining a known position of the cartridge 12 inside the cartridge holder 13 which may help to improve dosing accuracy.

When in reset configuration R it has to be noted that a proximally-directed force to be applied to the pressure piece 92 is typically less than the force exerted on the insert 50 by the reset spring 134. Therefore, during a proximal displacement of the piston rod 90 back into its proximal and initial position the insert 50 is kept in the distal reset position R by the reset spring 134. During displacement of the insert 50 from its proximal operating position O into its distal reset position R, the dispensing spring 130 is subject to at least a slight axial relaxation or axial extension. However, the force exerted by the dispensing spring 130 in proximal direction 2 onto the lock member 180 is still large enough to keep the dial sleeve 140 in rotational engagement with the body 65 through the mutually mating detent structures 141, 69.

LIST OF REFERENCE NUMBERS 1 distal direction
2 proximal direction
3 rotation axis
4 axial direction
5 dose incrementing direction
6 dose decrementing direction
7 coupling axis
10 injection device
11 medicament
12 cartridge
13 cartridge holder
14 piston
15 fastening structure
16 socket
18 drive mechanism
20 display arrangement
22 first display member 23 body
24 second display member
25 geared section
26 coupling member
28 display surface
32 cam
37 shaft
38 geared section
40 shaft
42 first geared section
44 second geared section
50 insert
51 distal end
52 thread
53 proximal end
54 through opening
55 fastening portion
55a surface
56 groove
57 disc portion
58 sidewall portion
60 housing
61 fastening structure
62 window
63 cover
64 receptacle
65 body
66 flange portion
67 stop
68 recess
69 toothed portion
70 inlay
72 bearing
80 insert
81 groove
82 toothed structure
90 piston rod
91 outer thread
92 pressure piece
94 groove
100 dose setting member
101 detent structure
102 protrusion
103 flange portion
104 protrusion
105 dose button
106 end face
107 bulged portion
108 recess
109 stop face
110 drive sleeve
111 protrusion
112 detent structure
114 detent structure
115 flange portion
116 recessed portion
117 threaded section
118 axial connection
120 last dose limiting mechanism
122 last dose limiting member
124 stop member
125 protrusion
130 dispensing spring
134 reset spring
136 drive spring
138 sidewall portion
139 receptacle
140 dial sleeve
141 toothed portion
142 groove
143 distal portion
143a detent structure
143b flange portion
144 neck portion
145 proximal portion
146 threaded section
147 stop
148 stop
149 detent structure
150 single dose limiting member
152 threaded section
154 protrusion
160 ring gear
162 detent structure
163 radially widened portion
164 geared structure
170 planet gear
180 lock member
181 protrusion
182 detent structure
183 proximal end
184 abutment surface
190 clicking member
194 nose portion
196 bulged portion
200 reset mechanism

The invention claimed is:

1. A drive mechanism of an injection device for setting and dispensing of a dose of a medicament, the drive mechanism comprising:
a body extending in an axial direction to accommodate a cartridge filled with the medicament or being connectable with a cartridge holder to accommodate the cartridge,
an insert axially displaceable inside the body between a proximal operating position and a distal reset position, wherein the insert is axially slidably arranged inside the body towards the proximal operating position against an action of a reset spring, the reset spring being operable to move the insert into the distal reset position,
a piston rod configured to operably engage with a piston of the cartridge, wherein the piston rod extends in the axial direction and is threadedly engaged with the insert,
a drive sleeve rotationally coupled with the piston rod and extending in the axial direction, and
a lock member radially arranged between the drive sleeve and the body and being permanently rotationally locked to the body,
wherein the drive sleeve is (i) rotationally lockable to the lock member for setting of the dose, (ii) rotationally releasable from the lock member for dispensing of the dose, (iii) axially connected to the insert, (iv) displaceable relative to the lock member from a proximal operating position into a distal reset position under the action of the reset spring, and (v) rotationally released from the lock member when the drive sleeve is in the distal reset position.

2. The drive mechanism according to claim 1, wherein the drive sleeve is rotatable relative to the insert.

3. The drive mechanism according to claim 1, wherein the reset spring is located axially between the insert and a radially inwardly facing flange portion of the body.

4. The drive mechanism according to claim 1, wherein the lock member is axially displaceable relative to the body between a proximal dose setting position and a distal dose dispensing position.

5. The drive mechanism according to claim 4, wherein the drive sleeve is configured to be rotationally engaged with the lock member when the drive sleeve is in the proximal operating position and when the lock member is in the proximal dose setting position.

6. The drive mechanism according to claim 5, wherein the lock member is of annular shape and comprises an annular detent structure at an inward-facing sidewall portion, and the annular detent structure is configured to engage with a first annular detent structure on an outer circumference of the drive sleeve when the lock member is in the proximal dose setting position and when the drive sleeve is in the proximal operating position.

7. The drive mechanism according to claim 4, wherein the drive sleeve is configured to be rotationally released from the lock member when the drive sleeve is in the proximal operating position and when the lock member is in the distal dose dispensing position.

8. The drive mechanism according to claim 1, wherein the lock member is axially displaceable relative to the body in a distal direction against an action of a dispensing spring.

9. The drive mechanism according to claim 8, wherein a distal end of the dispensing spring is supported by or is connected with the insert and wherein a proximal end of the dispensing spring is supported by or is connected with the lock member.

10. The drive mechanism according to claim 1, wherein the insert is configured to be axially fixed inside the body by an axial abutment with the cartridge or by an axial abutment with the cartridge holder accommodating the cartridge.

11. The drive mechanism according to claim 1, comprising a dial sleeve rotatable inside the body in a dose incrementing direction against an action of a drive spring, wherein the dial sleeve is axially displaceable relative to the body between a distal dose dispensing position and a proximal dose setting position.

12. The drive mechanism according to claim 11, wherein the dial sleeve is configured to axially abut the lock member to displace the lock member from a dose setting position into a dose dispensing position.

13. The drive mechanism according to claim 11, wherein the dial sleeve is configured to be rotationally engaged with the drive sleeve when the dial sleeve is in the distal dose dispensing position and when the drive sleeve is in the proximal operating position.

14. The drive mechanism according to claim 11, wherein the drive sleeve is configured to be rotationally released from the dial sleeve when the dial sleeve is in the proximal dose setting position.

15. The drive mechanism according to claim 11, wherein the drive sleeve is configured to be rotationally released from the dial sleeve when the drive sleeve is in the distal reset position.

16. The drive mechanism according to claim 1, wherein the insert is splined to the body.

17. The drive mechanism according to claim 1, wherein a distal end of the reset spring axially abuts a proximal end of the insert, and a proximal end of the reset spring axially abuts the body.

18. An injection device for dispensing of a dose of a medicament, the injection device comprising:
a cartridge at least partially filled with the medicament; and
a drive mechanism comprising:
a body extending in an axial direction to accommodate the cartridge or connectable with a cartridge holder to accommodate the cartridge,
an insert axially displaceable inside the body between a proximal operating position and a distal reset position, wherein the insert is axially slidably arranged inside the body towards the proximal operating position against an action of a reset spring, the reset spring being operable to move the insert into the distal reset position,
a piston rod configured to operably engage with a piston of the cartridge, wherein the piston rod extends in axial direction and is threadedly engaged with the insert,
a drive sleeve rotationally coupled with the piston rod and extending in axial direction, and
a lock member radially arranged between the drive sleeve and the body and being permanently rotationally locked to the body,
wherein the drive sleeve is rotationally lockable to the lock member for setting of the dose and wherein the drive sleeve is rotationally releasable from the lock member for dispensing of the dose, and
wherein the drive sleeve is (i) axially connected to the insert, (ii) displaceable relative to the lock member from a proximal operating position into a distal reset position under the action of the reset spring, and (iii) rotationally released from the lock member when the drive sleeve is in the distal reset position,
wherein the cartridge is arranged in the body of the drive mechanism or in the cartridge holder, the cartridge holder being connected to the body or configured to be connected to the body.

19. The injection device of claim 18, wherein the medicament comprises a pharmaceutically active compound.

* * * * *